US010835159B2

(12) United States Patent
Schabel et al.

(10) Patent No.: US 10,835,159 B2
(45) Date of Patent: Nov. 17, 2020

(54) SYSTEMS AND METHODS FOR FUNCTIONAL IMAGING OF THE PLACENTA

(71) Applicants: Matthias Schabel, Portland, OR (US); Antonio Frias, Portland, OR (US); Christopher Kroenke, Portland, OR (US)

(72) Inventors: Matthias Schabel, Portland, OR (US); Antonio Frias, Portland, OR (US); Christopher Kroenke, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 453 days.

(21) Appl. No.: 15/274,718

(22) Filed: Sep. 23, 2016

(65) Prior Publication Data

US 2017/0086720 A1 Mar. 30, 2017

Related U.S. Application Data

(60) Provisional application No. 62/232,955, filed on Sep. 25, 2015.

(51) Int. Cl.
*A61B 5/145* (2006.01)
*A61B 5/00* (2006.01)
(Continued)

(52) U.S. Cl.
CPC ........ *A61B 5/14542* (2013.01); *A61B 5/0263* (2013.01); *A61B 5/055* (2013.01);
(Continued)

(58) Field of Classification Search
None
See application file for complete search history.

(56) References Cited

U.S. PATENT DOCUMENTS

| 6,605,943 B1 * | 8/2003 | Clark | G01R 33/50 |
| | | | 324/309 |
| 8,958,866 B2 * | 2/2015 | Bolar | A61B 5/055 |
| | | | 324/309 |

(Continued)

OTHER PUBLICATIONS

Solomon et al. Major mouse placental compartments revealed by diffusion-weighted MRI, contrast-enhanced MRI, and fluorescence imaging (2014), PNAS 111 (28): 10353-10358 (Year: 2014).*
Solomon et al. (2014). Major mouse placental compartments revealed by diffusion-weighted MRI, contrast-enhanced MRI, and fluorescence imaging, PNAS 111 (28): 10353-10358 (Year: 2014).*
Varghese et al. Magnetic resonance imaging of placenta accreta (2013). Indian J Radiol Imaging. 23:379-85. (Year: 2013).*

*Primary Examiner* — Patricia J Park
*Assistant Examiner* — Younhee Choi

(57) ABSTRACT

A method or system for imaging and quantifying placental blood perfusion using magnetic resonance image. The method or system provides a noninvasive means of assessing placental function and oxygenation from $T_2^*$ images without the administration of an exogenous contrast agent. The method or system provides quantitative information regarding the number and spatial distribution of perfusion domains which subdivide the placenta into functional units where oxygen transport occurs, along with estimates of fetal oxyhemoglobin concentration, descriptors of placental oxygen reserve, and parameters representing the facility with which oxygen transport from the maternal to fetal vasculature occurs.

15 Claims, 12 Drawing Sheets

(51) Int. Cl.
    *G01R 33/50*     (2006.01)
    *G06F 30/20*     (2020.01)
    *G01R 33/56*     (2006.01)
    *A61B 5/026*     (2006.01)
    *A61B 5/055*     (2006.01)
    *G01R 33/561*     (2006.01)
    *G01R 33/563*     (2006.01)

(52) U.S. Cl.
    CPC ........ *A61B 5/14546* (2013.01); *A61B 5/4343* (2013.01); *A61B 5/4362* (2013.01); *A61B 5/7278* (2013.01); *G01R 33/50* (2013.01); *G01R 33/5608* (2013.01); *G01R 33/5616* (2013.01); *G01R 33/56366* (2013.01); *G06F 30/20* (2020.01)

(56) References Cited

U.S. PATENT DOCUMENTS

| | | | |
|---|---|---|---|
| 9,134,394 B2 * | 9/2015 | Miyazaki | A61B 5/055 |
| 2015/0359475 A1 * | 12/2015 | Bennett | A61B 5/201 |
| | | | 600/420 |
| 2016/0005183 A1 * | 1/2016 | Thiagarajan | A61B 5/055 |
| | | | 382/131 |
| 2016/0349339 A1 * | 12/2016 | Brady-Kalnay | G01R 33/50 |
| 2017/0049379 A1 * | 2/2017 | Luo | A61B 5/14542 |

* cited by examiner

SYSTEMS AND METHODS FOR FUNCTIONAL IMAGING OF THE PLACENTA

ACKNOWLEDGEMENT OF GOVERNMENT SUPPORT

This invention was made with government support under HD076265 and DK090964 awarded by the National Institutes of Health. The government has certain rights in the invention.

FIELD

Generally, the field is imaging of tissue using magnetic resonance imaging. More specifically, systems and methods are presented for imaging and quantifying placental function and perfusion by magnetic resonance imaging without the use of exogenous contrast reagents.

BACKGROUND

There is tremendous clinical need for non-invasive tools for in vivo assessment of maternal blood flow and oxygen delivery within the placenta. Many aspects of placental growth, development, and function are incompletely understood despite the crucial role this organ plays in regulating maternal-fetal exchange of oxygen, nutrients, and waste products. Impairment of placental function is implicated in a range of adverse outcomes including, for example, preeclampsia, pre-term labor, and intrauterine growth restriction (Kidron D et al, *Placenta* 30, 700-704, (2009); Roberts D et al, *J Clin Pathol* 61, 1254-60 (2008); Salafia C et al, *Am J Perinatol* 9, 179-84 (1992); Salafia C et al, *Am J Perinatol* 9, 190-3 (1992); incorporated by reference herein). However, an understanding of the specific role of placental pathophysiology is limited by the inability, at present, to characterize maternal placental blood flow in the clinical context.

A particular limitation of current non-invasive clinical tools for assessing placental function (e.g. Doppler ultrasound) is that they are incapable of characterizing perfusion within the intervillous space, the site of oxygen exchange between the maternal and fetal vasculature. Rather, these techniques are directed at the major vessels supporting the placenta. Furthermore, MRI indications in human pregnancy generally focus on assessment of fetal developmental abnormalities, while the characterization of aberrant placental development receives less focus (Palacios-Jaraquemada J, et al, *Acta Obstet Gynecol Scand* 92, 392-397 (2013); Lyendecker J, et al, *AJR Am J Roentgenol* 198, 311-320 (2012); Podrasky A, et al, *Ultrasound Q* 29, 293-301 (2013); Levine D, et al, *Radiology* 205, 773-776 (1997); incorporated by reference herein). Approaches such as dynamic contrast-enhanced MRI (DCE-MRI) do provide a potential method to characterize maternal blood flow in intervillous spaces, but such measurements require the injection of a contrast reagent (CR) into the maternal vasculature and therefore raise concerns about possible effects of the CR on the fetus. It has been reported, however, that one such CR, gadolinium chelate (Prohance®), has limited transplacental passage, minimizing fetal tissue exposure and suggesting that the risk of adverse fetal effects is low (Oh, K, et al, *Radiology* 275, 110-118 (2015); incorporated by reference herein). In addition, contrast-enhanced imaging has been reported for evaluation of cases of placenta accrete (Palacios-Jaraquemada J, et al, *Radiology* 216, 610-611 (2000); incorporated by reference herein). Nevertheless, lingering uncertainties about consequences of fetal CR exposure make it unlikely that gadolinium-based CR will be used routinely for in vivo investigation of placental function in pregnant women. Thus, there is an unmet need for quantitative methods that allow measurement of placental oxygen delivery and transport between the maternal and fetal vasculatures.

SUMMARY

The present disclosure is directed to systems and methods for quantification of placental structure and placental function. More specifically, the aim of the invention described herein is to provide a method for analyzing MRI-based $T_2^*$-weighted images of the placenta to estimate a number of parameters which directly relate to maternal blood flow into the placenta and perfusion of the intervillous space contained therein. These parameters can provide, for example, a noninvasive estimate of fetal oxyhemoglobin concentration, as well as structural and functional metrics that reflect the placenta's ability to provide oxygenated blood from the maternal to the fetal vasculature. As such, the disclosed methods can provide important clinical indicators of fetal health status and development.

An important aspect of the methods disclosed herein is that they do not require the use of a CR during image acquisition. Hence, the potentially harmful effects of fetal exposure to CR during MRI imaging are eliminated using the disclosed methods. A further aspect of these CR-free methods is that they may be used in conjunction with other methods that do utilize CR, for example DCE-MRI, to further elucidate structural-functional characteristics of placental perfusion.

It is an aim of the disclosed systems and methods to quantify the overall oxygen perfusion of the placenta. In embodiments, the endogenous oxyhemoglobin-deoxyhemoglobin contrast contained in acquired MRI data is used to compute maps of transverse relaxation time ($T_2^*$ or $T_2$, for example). The maps can be used, in some embodiments, to calculate statistics that estimate the sufficiency of the maternal placental blood supply to provide oxygenated blood for consumption by the fetus at different gestational ages and under various developmental stressors.

It is also an aim of the disclosed methods to identify by both location and number the multiplicity of maternal spiral artery inflow sites which supply the placenta with oxygenated blood from the maternal vasculature. Further, based on the identification of these inflow sites, methods are disclosed to partition the placenta into a set of functional perfusion domains, termed lobules, each lobule being supplied by its own spiral artery input source. The organization, multiplicity, shape, and volume characteristics of these lobules further provide structural metrics which can be used to characterize, for example, placental growth development.

As disclosed herein, the delineation of functional perfusion domains further enables assessment of placental function by application of a mathematical model of maternal-fetal oxygen transport describing the spatial dependence of oxyhemoglobin-deoxyhemoglobin contrast within individual lobules. In embodiments described herein, parameters recovered from such a mathematical model can provide insight into various aspects of placental function such as fetal oxyhemoglobin concentration and oxyhemoglobin transport at the interface between maternal and fetal vasculature within individual lobules.

An aspect of the disclosed methods is that any clinical MRI machine capable of acquiring images at multiple echo times is suitable for use with the analysis techniques described herein. Further, the disclosed methods are applicable to MRI data acquired in either 2-D or 3-D imaging modes.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that solve any or all disadvantages noted in any part of this disclosure.

BRIEF DESCRIPTION OF THE SEVERAL VIEWS OF THE DRAWINGS

Embodiments will be readily understood by the following detailed description in conjunction with the accompanying drawings. Embodiments are illustrated by way of example and not by way of limitation in the figures of the accompanying drawings

(solid line) and G135 (dashed line). Protein restricted animals had a smaller fraction of large $T_2^*$ values compared to controls, demonstrating decreased fetal oxygen supply in the former group.

Figure 11:
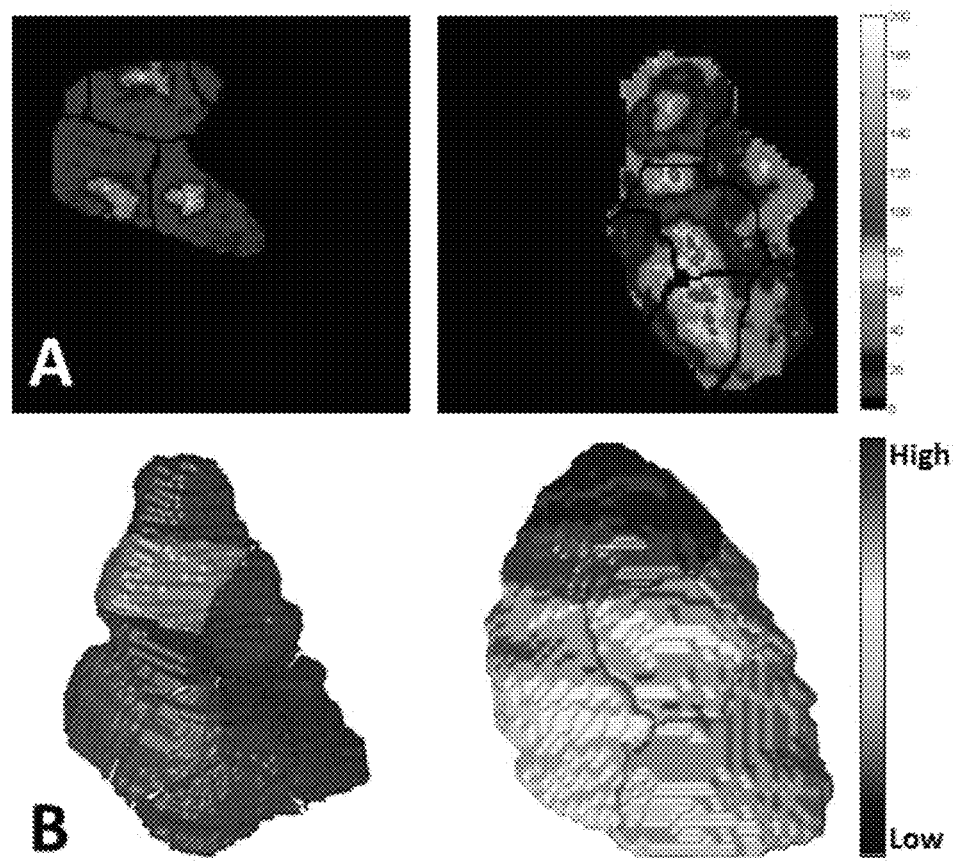

FIG. 11 is a panel of images showing MRI results of a control (left) and an ethanol exposed (right) animal. Panel (A) shows multiecho $T_2^*$ imaging for a single imaging slice through the primary placental lobe. The scale is from 0 to 200 ms. Panel (B) shows volume renderings depicting the spiral artery flow differences ($\Psi_j$) by cotyledon color coded according to volumetric flow rates.

Figure 12:
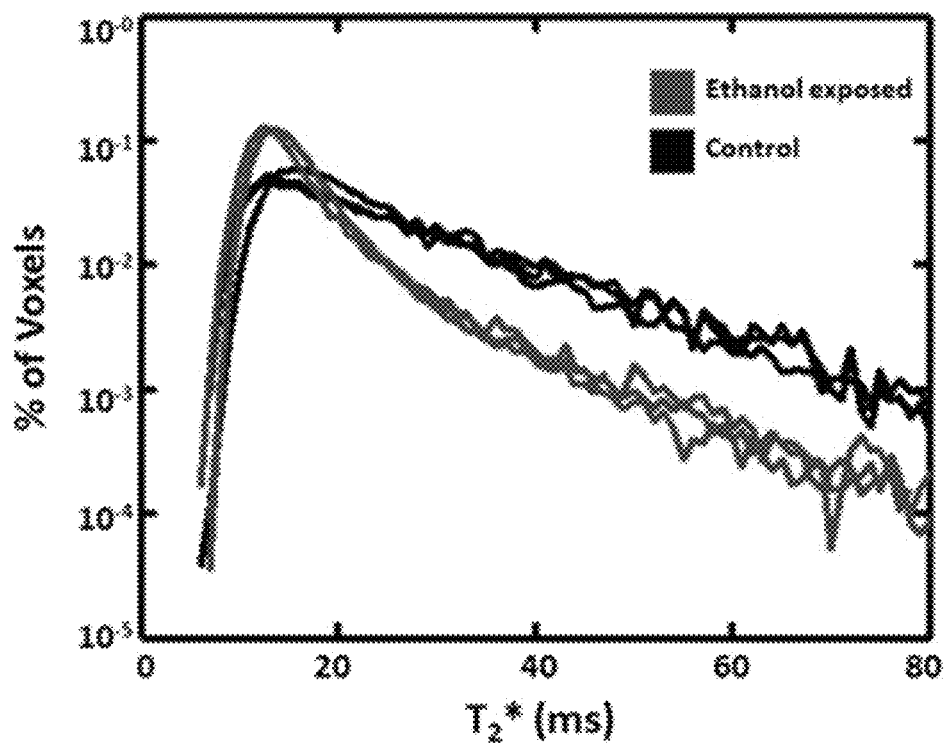

FIG. 12 is a histogram plot of $T_2^*$ versus percent of voxels displayed for ethanol exposed versus control animals.

Figure 13:
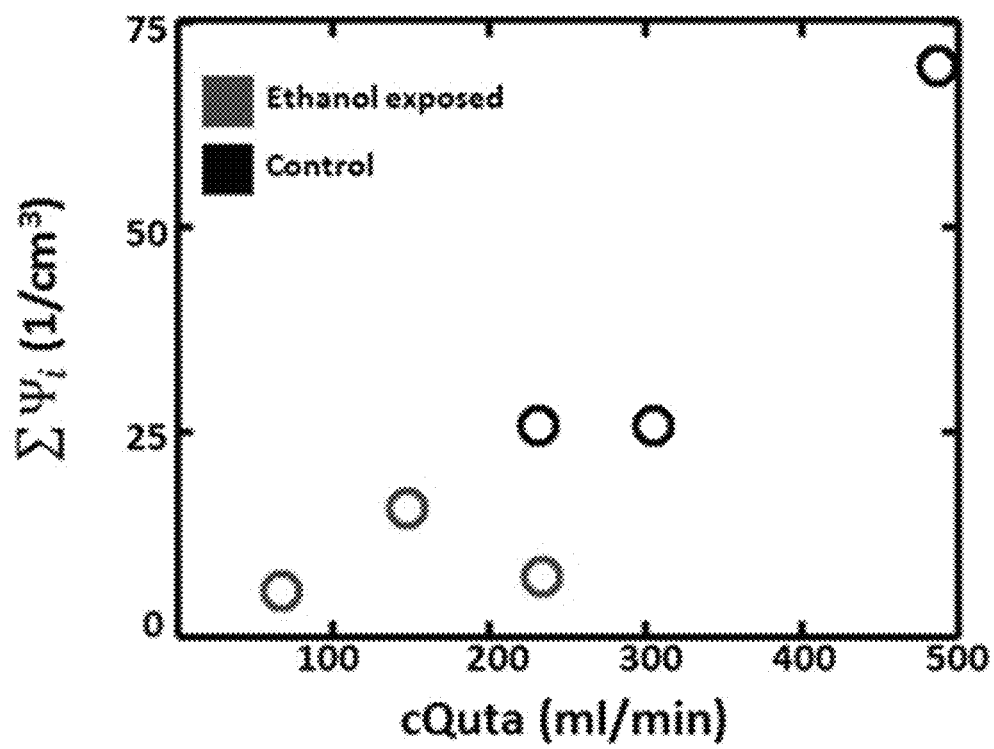

FIG. 13 is a plot showing the correlation between ultrasound and MRI findings for ethanol exposed versus control animals, r=0.91 (p=0.01).

Figure 14:
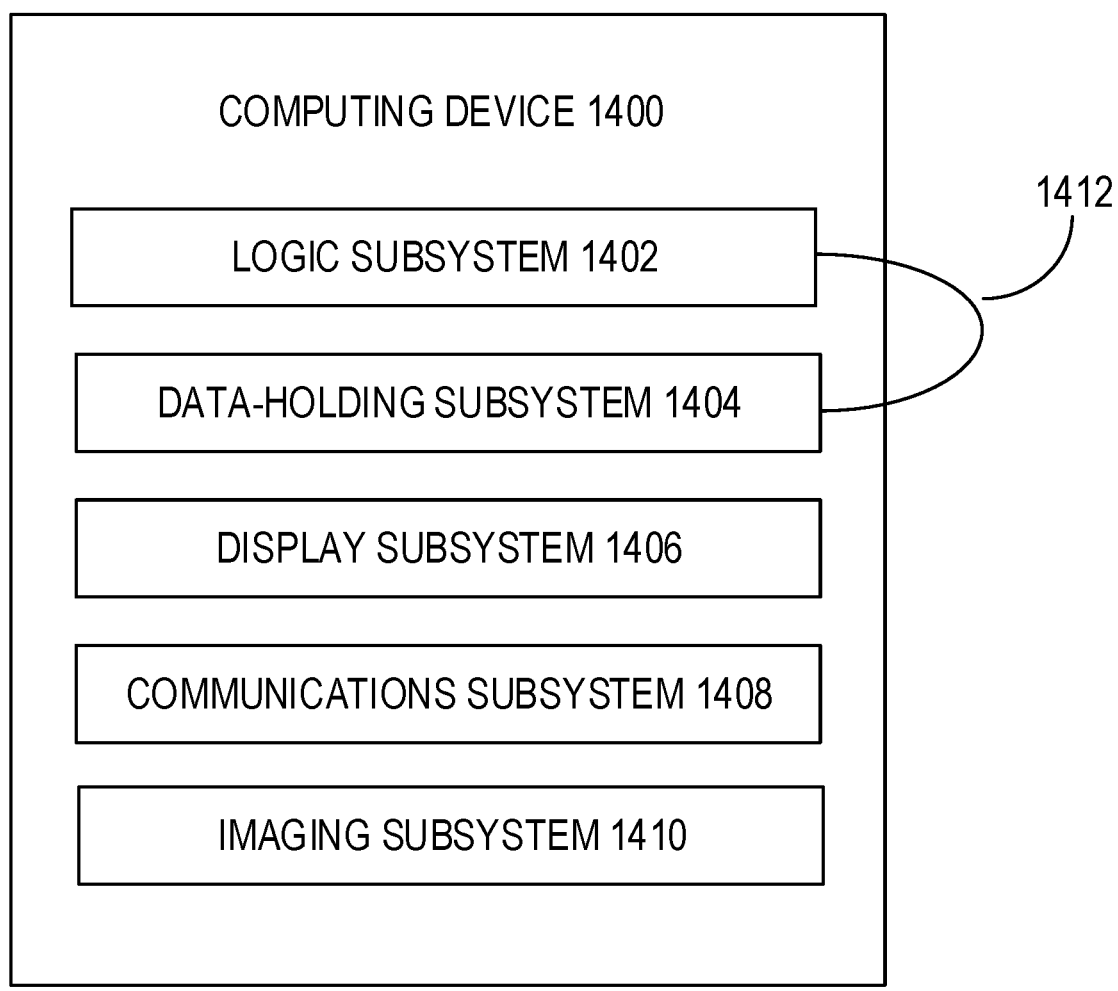

FIG. 14 schematically shows an example computing system in accordance with the disclosure.

DETAILED DESCRIPTION

The following detailed description is directed to systems and methods for quantifying placental structure and function. In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the present invention, the phrase "A/B" means A or B. For the purposes of the present invention, the phrase "A and/or B" means "(A), (B), or (A and B)". For the purposes of the present invention, the phrase "at least one of A, B, and C" means "(A), (B), (C), (A and B), (A and C), (B and C), or (A, B and C)". For the purposes of the present invention, the phrase "(A)B" means "(B) or (AB)" that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

In various embodiments, methods, apparatuses, and systems and for measuring placental function and perfusion are provided. In exemplary embodiments, a computing device may be endowed with one or more components of the disclosed apparatuses and/or systems and may be employed to perform one or more methods as disclosed herein.

Embodiments herein provide a magnetic resonance imaging (MRI) technique to analyze image data of the developing placenta during pregnancy. In one aspect of the disclosed embodiments, methods are provide that allow characterization of the overall perfusion status of the placenta with regard to balance of maternal provision of oxygenated blood and fetal consumption thereof. In another aspect of the disclosed embodiments, methods are provided that allow characterization of the structural organization of the placenta reflecting the underlying functional anatomy. In another aspect, this structural information can be used in concert with acquired imaging data to quantify placental function at the interface between the maternal and fetal vasculature. As used herein, placental function refers to perfusion of the intervillous spaces of the placenta with maternal blood, the transport of oxygen and nutrients from the maternal to the fetal blood supply, and the transport of carbon dioxide and waste products back to the maternal blood supply.

An important aspect of the methods described herein is that they may be performed without the use of a contrast reagent (although in some embodiments a contrast agent may also be used, for example, to provide additional data for interpretation of results). Instead the method exploits the endogenous blood oxygen level dependent (BOLD) effect to map the spatial distribution of oxygenated maternal blood within functional perfusion domains distributed within the placenta. In a particular embodiment described in the examples below, the spatial distribution of $T_2^*$ measurements and associated $R_2^*$ ($=1/T_2^*$) are used. However, the method is not strictly limited to $T_2^*$ images as input; any imaging modality that provides oxyhemoglobin-deoxyhemoglobin contrast can be used with the proposed method, including, for example, $T_1$ and $T_2$ datasets.

In an embodiment, CR-free mapping of the spatial distribution of placental $T_2^*$ values can be used to quantify placental structure and function. For example, the spatial maps of $T_2^*$ can be converted into ratios of maternal oxyhemoglobin concentration to total maternal hemoglobin concentration (or other mathematical expressions utilizing the relationship between placental oxyhemoglobin/deoxyhemoglobin ratio and $T_2^*$ or other oxygen-sensitive MRI parameters); when this value is large, it indicates that an excess of oxygenated maternal blood relative to fetal oxygen consumption is being supplied, and when it is small it indicates that the bulk of the maternal supply of oxygen is consumed by the fetus. Such an indicator of the relative balance between maternal supply of oxygenated blood and fetal consumption underlies the concept of placental oxygen reserve (POR), and represents the capacity (or incapacity) of the maternal placental blood supply to provide oxygenated blood for consumption by the fetus at any gestational age.

As another example, in a spatial mapping of $T_2^*$ values, locations of $T_2^*$ maxima can be identified within regions of relatively long $T_2^*$ surrounded by a penumbra of shorter $T_2^*$. The locations of these $T_2^*$ maxima closely correspond with spatial locations of spiral artery sources of maternal blood perfusing the placenta (as demonstrated in Example 1, below). In the methods disclosed herein, this correspondence is exploited to partition the placenta into distinct perfusion domains (also termed "lobules"), each supplied by its own spiral artery input, and each perfusion domain reflecting the structural-functional organization placental anatomy. These perfusion domains represent the functional boundaries of perfusion within partitions of the placenta, where maternal blood supplied at the spiral artery inflow location traverses and bathes the intervillous space to effect oxygen transport to the fetal vasculature.

In embodiments, perfusion domains can be determined using a computational surface evolution approach wherein each inflow site serves as a seed point to initialize a surface evolution algorithm. The algorithm is used to iteratively propagate from the seed points an outward-growing wavefront that ultimately defines the bounding volumes associated with each perfusion domain. The intermediate iterations of the evolution algorithm provide a representation of the diffusion of blood passing from the inflow sites to the intervillous space, and can be used to link spatial variation of endogenous contrast to a distance metric quantifying separation from the site of blood inflow. In terms of implementation, this iterative delineation of perfusion volumes can be accomplished using a multistencil fast-marching method, a level set method, active contours, or other surface evolution methods. Once $T_2^*$ maps have been partitioned (e.g. by using a watershed algorithm or other method for separating spatial domains via distance metric), structural indices such as individual lobule volumes can be calculated to characterize placental functional anatomy. Such indices can be used to track developmental changes or identify normal or anomalous placental structure. For example, in embodiments, the number of individual lobules and their volumes can be compared to ranges for a normal population as an indicator of placental development. In another example, a comparison of total lobule volume to total placenta volume (as determined from a segmentation of the placenta boundaries within the MRI scan volume, for example) can be used as an indicator of functional efficiency. Similarly, the number and spacing of lobules and/or their inflow sites can provide indicators of placental health, function, or dysfunction when compared to ranges for a normal population.

In a further embodiment, the delineation of functional perfusion domains can be used to assess placental function by application of a mathematical model of oxygen transport describing, for example, the spatial dependence of $R_2^*$ within individual lobules. For example, in an embodiment disclosed herein, a model is presented which allows quantitative estimates of fetal oxyhemoglobin concentration $[Hb_{o,f}]$ along with a parameter $v_iPS/\Phi$. The latter parameter, $v_iPS/\Phi$, is described in detail in Example 1 below. Briefly, it a composite parameter which reflects the ability of oxygen to transport from the intervillous space to the fetus by combining the effects of permeability, permeable surface area for transport, fraction of intervillous space in the lobule, and blood flow rate into the lobule. Those skilled in the art will recognize that more sophisticated models, for example 3D models such as those based on finite difference or finite element methods, or other methods of solving the underlying partial differential equations describing the spatial distribution of oxyhemoglobin distribution, can also be developed to relate lobule-level $R_2^*$ spatial data to functionally relevant perfusion and transport parameters.

In yet another embodiment, the disclosed CR-free methods can be used in conjunction with CR-based methods such as DCE-MRI to augment the information obtained using the disclosed methods. Without the use of CR, some of the methods described herein are unable to separately differentiate between the effects of changes in fetal villous oxygen permeability-surface area product (PS), placental intervillous volume ($v_i$), or spiral artery blood flow ($\Phi$). By addition of CR via DCE-MRI or other indicator-dilution type measurement, via MRI or other modality, it is possible to separately assess $v_i$ and $\Phi$, consequently enabling the determination of PS. Via such methods it is possible to identify placental deficiencies stemming from alteration in the fetal villous tree and discriminate these from placental deficiencies stemming from inadequate maternal placental blood supply and/or decreased intervillous volume.

Figure 2:
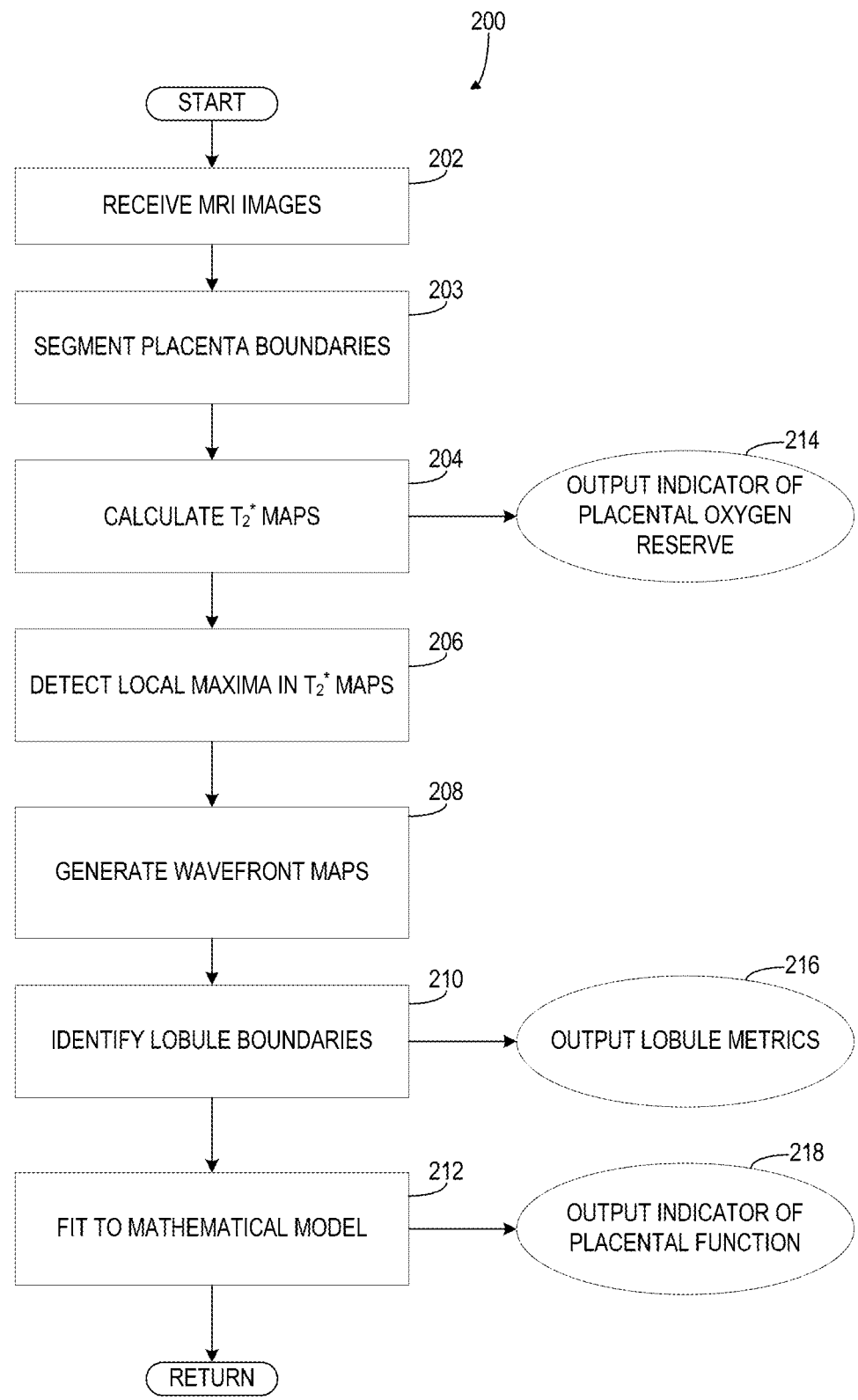
FIG. 2 shows an example method for quantification of placental function in accordance with the disclosure.

FIG. 2 shows an example of a method 200 to analyze MRI data using the methods disclosed herein. Method 200 may be used, for example, to calculate structural and functional characteristics of the placenta within a living subject to assess placental health and/or development. One or more steps of method 200 may be performed by one or more computing devices, such as the computing device described below with regard to FIG. 14. Such computing devices may comprise an MRI data acquisition system, one or more processors included in an MRI system, one or more image processors, and/or any other suitable processors which include physical circuitry programmed to automatically perform steps of method 100. It should be understood that the various acts illustrated in method 200 may be performed in the sequence illustrated, in other sequences, in parallel, or in some cases omitted.

At 202, an MRI dataset is received in method 200. This dataset may comprise any MRI imaging sequence acquired with multiple echo times or sequences that are sensitive to changes in the ratio of oxyhemoglobin to deoxyhemoglobin in placental blood, including, but not limited to, $T_2^*$, $T_2$, or $T_1$. At 203, the outer boundaries of the placenta are delineated using an automated, semi-automated, or manual segmentation method known in the art. Depending on the application, either 2D or 3D segmentation may be performed. At 204, the MRI voxel data bounded by the placenta segmentation are converted into $T_2^*$ maps to reflect the spatial variation of oxyhemoglobin-deoxyhemoglobin concentration therein. In embodiments, MRI data may also be mapped, for example, as $T_2$ values or in other formats which indicate oxyhemoglobin-deoxyhemoglobin contrast within the region of interest.

From the $T_2^*$ maps generated at 204, a plurality of local maxima (or minima, as appropriate) are detected at 206. These local maxima, as noted above, correspond with the spatial locations of spiral artery sources of maternal blood entering the placenta. In embodiments described herein, these local maxima are used as seed points from which perfusion domains are identified. At 208, an advancing-front-type segmentation algorithm is used to propagate an outward-growing wavefront from each of said plurality of seed points in a step-wise manner. The set of intermediate wavefronts associated with each of the seed points are used to generate wavefront maps at 208 that reflect the iterative evolution the segmentation surface. The final set of wavefronts from the surface evolution segmentation are used at 210 to identify lobule boundaries, thus partitioning the placenta into a plurality of perfusion domains associated with each of the plurality of spiral artery sources.

At 212, the $T_2^*$ maps of 204 and the wavefront maps of 208 are used in the fitting of a mathematical model representing an idealized situation in which oxygenated maternal blood flows from a spiral artery into a placental lobule, is transported past a fetal villous tree where exchange of oxygen and other compounds occurs between maternal and fetal blood, and then is returned to the maternal circulation. Such models may vary in fidelity and simplicity, ranging from the simple 1-dimensional model described in Example 1 below to models that approximate or solve the complete system of 3-dimensional coupled partial differential equations for lobular structures and geometries modeled at various levels of fidelity. Such solution methods may include finite element, finite volume, or other analytical or numerical methods for the solution of systems of partial differential equations. At 214, statistics characterizing the relative ratios of oxygenated maternal blood to deoxygenated maternal blood within the placenta are computed. These statistics allow assessment of the adequacy of maternal supply of oxygenated blood to the fetus via the placenta relative to the total fetal consumption of oxygen from said maternal blood supply (the concept of placental oxygen reserve). Such statistics could include, but are not limited to, integrals or histograms of $T_2^*$, $R_2^*$, maternal oxyhemoglobin concentration, or the ratio of maternal oxyhemoglobin to total maternal hemoglobin.

At 216, statistics characterizing the spatial structure of lobules are computed. Such statistics may include total number of lobules, lobule surface area, lobule volume, lobule morphology as measured by various descriptors such as, but not limited to, surface area to volume ratio, fractal dimension, roughness, etc. Spatial regions of hypoperfusion may also be mapped, as can infarcted (nonfunctional) placental tissues.

At 218, parameters derived from the mathematical model at 212 are output. These parameters may include quantitative estimates of fetal oxyhemoglobin concentration, indicators of permeability and transport at the permeable surface separating maternal and fetal blood supply, blood flow rate into the lobule, or other indicators, depending on the specific formulation of the mathematical model.

It is also noted that any clinical MRI machine capable of acquiring images at multiple echo times is suitable for the method described herein, and that data may be acquired in either 2-D or 3-D imaging modes. In one embodiment, an MRI machine equipped for spoiled gradient echo (SPGR) pulse sequences may be used to acquire multi-slice image data for analysis by the disclosed method. Alternatively, single-shot turbo spin-echo (HASTE) acquisition may be used. Those skilled in the art will recognize other MRI image acquisition modalities that provide oxyhemoglobin-deoxyhemoglobin contrast information that can be used in conjunction with the methods described herein.

EXAMPLES

Example 1

Methods for Spatial Modeling of $T_2^*$ Distributions and Quantifying Placental Structure and Function The following example demonstrates the use of a number of embodiments of the the disclosed methods to characterize the transverse relaxation time in the primate placenta ($T_2^*$). As part of this demonstration, the anatomical results obtained using the disclosed methods are shown to correlate with those obtained using DCE-MRI, a CR-based imaging method.

Anatomic Structure of the Primate Placenta

Figure 1:
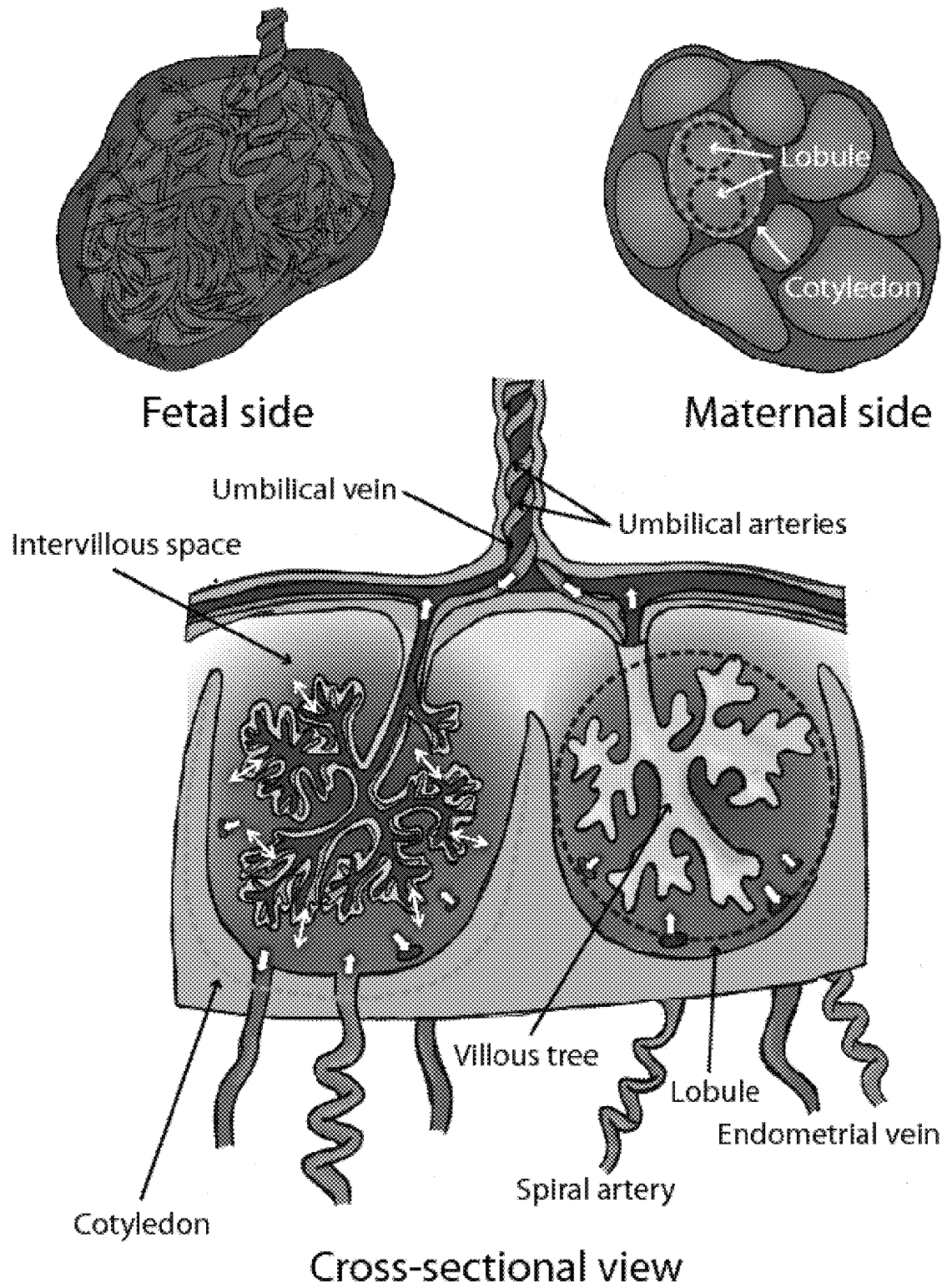
FIG. 1 depicts a schematic illustration of the anatomy and morphology of the primate placenta showing both the maternal and fetal surfaces, along with a cross-sectional view.

The hemochorial structure of the primate placenta, in which maternal blood of the intervillous space bathes villi containing fetal blood vessels, ties placental vascular organization to maternal-fetal oxygen transport. A schematic illustration of the primate placenta is shown in FIG. 1, identifying major structures including umbilical arteries, umbilical vein, cotyledons, lobules, villous tree, spiral arteries, and endometrial veins. Oxygenated maternal blood is supplied to the placenta via spiral arteries, which branch from the uterine arteries, terminating in anatomic structures termed cotyledons. Oxygen, nutrients, and wastes are exchanged between the maternal blood occupying the intervillous space and the fetal capillaries comprising the villous tree, as indicated in FIG. 1 by the double headed white arrows.

The correspondence between spiral arteries and cotyledons is not consistently one-to-one, with some cotyledons perfused by two or more spiral arteries (Frias A, et al, *Magn Reson Med* 73, 1570-1578 (2015); incorporated herein by reference). In order to clarify terminology, the conventions of Faber and Thornburg are adopted (Faber J, et al, *Placental Physiology*, New York: Raven Press, 1983; incorporated herein by reference) by referring to the perfusion domain associated with a single spiral artery as a lobule. When a single spiral artery perfuses a cotyledon, the cotyledon and the lobule are identical, while cotyledons having multiple spiral artery sources will contain multiple associated lobules. Deoxygenated maternal blood is transported away from lobules via venous structures located at the lobular periphery. In humans, roughly 10-40 cotyledons are distributed within a single discoid placental lobe, with 1-4 lobules per cotyledon, each associated with a single spiral artery supplying maternal blood to the intervillous space (Faber J, et al, 1983 supra; Huppertz B, *J Clin Pathol* 61, 1296-1302 (2008); incorporated herein by reference). Rhesus macaques have a comparable number of cotyledons, typically distributed across two lobes of a bidiscoid placenta. Based on previous DCE-MRI studies, lobules typically have volumes on the order of 1-2 cm³. The intervillous space (the placental space accessible to maternal blood) constitutes approximately 40% of the total volume of a cotyledon, (Mayhew T, et al, *J Anat* 139, 691-708 (1984); incorporated by reference herein). Recently it has been established that dynamic contrast enhanced MRI (DCE-MRI), using bolus injection of a gadolinium-based contrast reagent (CR) into the maternal vasculature, can be used to delineate placental lobules by directly tracking the expanding wavefront of CR (Frias A E, et al, 2015 supra).

Methods of Data Acquisition

All procedures described in the following were approved by the Institutional Animal Care and Use Committee (IACUC) of the Oregon National Primate Research Center (ONPRC). The ONPRC abides by the Animal Welfare Act and regulations enforced by the U.S. Department of Agriculture, the Public Health Service Policy on Humane Care and Use of Laboratory Animals, in accordance with the U.S. National Institutes of Health Guide for the Care and Use of Laboratory Animals. Magnetic resonance imaging was performed on gestational day 110 (G110) in three pregnant rhesus macaques (*Macaca mulatta*, typical gestation of 168 days, referred to in this manuscript as animals A, B, and C) who were part of the control group in a study of fetal ethanol exposure. Animals were sedated by intramuscular administration of 10 mg/kg ketamine and intubated. Sedation was maintained by placing animals on a portable anesthesia delivery system providing $O_2$ with 1.5% isoflurane. Immediately prior to MRI, a catheter was placed in the saphenous vein for the delivery of the gadolinium-based contrast reagent.

MRI studies were performed on a nonhuman primate-dedicated 3T Siemens TIM-Trio scanner (Erlangen, Germany) using a circularly-polarized (CP) transmit, 15-channel receive radiofrequency (RF) "extremity" coil (QED, Cleveland, Ohio). Following localization of the placenta and acquisition of $T_2$-weighted half-Fourier acquisition single-shot turbo spin-echo (HASTE) anatomic images in the coronal and axial planes, axial 2D multislice spoiled gradient recalled echo (SPGR) images (TR=418 ms, flip angle=30°, 256×72 matrix, 96 slices, 1.5 mm isotropic spatial resolution), spanning the entire uterus, were acquired at six in-phase echo times (TE=4.92, 9.84, 19.68, 29.52, 36.90, and 44.28 ms) with monopolar readout gradients. Subsequently, 3D SPGR images were acquired in the coronal plane (TR=9.50 ms, TE=2.46 ms, 128×56×44 matrix, 2.5 mm isotropic spatial resolution, flip angles of 3° and 25°), also covering the entire uterus, to allow estimation of $T_1$ (longitudinal relaxation time) with the variable flip angle (VFA) method (Schabel M, et al, *Phys Med Biol* 54, N1-N8 (2009); incorporated by reference herein). Immediately after acquisition of VFA data, 150 volumes of 3D SPGR images were acquired for DCE-MRI (TR=2.00 ms, TE=0.72 ms, flip angle=20°, 6/8 partial Fourier encoding in both phase and slab encode directions, elliptical phase undersampling, parallel imaging with GRAPPA (iPAT factor of 2), acquisition time per frame of 3.64 seconds), with field of view and resolution matched to the VFA images. Ten baseline images were acquired prior to intravenous injection of a standard dose of 0.1 mmol/kg of gadoteridol CR (Prohance, Bracco Diagnostics Inc, Princeton, N.J.) at a rate of 30 mL/min using a syringe pump (Harvard Apparatus, Holliston, Mass.). Anatomic and multiecho imaging was performed during expiratory breath-holding, achieved by temporarily suspending ventilation, while DCE-MRI data were acquired during ventilation. Physiological monitoring of pulse rate, arterial blood oxygen saturation, and respiration rate was performed throughout the imaging study, with no deviations from normal ranges observed in these parameters for any of the three animals studied. Each physiological parameter was recorded at 10 minute intervals, and values reported herein are averages over the final 40 minutes of the MRI exam, which overlapped the time period in which placental multiecho and DCE-MRI data were collected. Immediately following each MRI procedure, fetuses were delivered by Cesarean section, and samples of maternal and fetal blood were collected for determinations of blood hemoglobin concentrations using a Pentra 60 C+ blood analyzer (HORIBA Medical, Irvine, Calif.).

$T_2^*$ Analysis

Spatial maps of the water $^1H$ transverse relaxation time ($T_2^*$) were computed per-voxel from multiecho SPGR measurements using a weighted linear least squares algorithm, implemented in MATLAB (Mathworks, Natick, Mass.), fitting the signal, S, to the linearized signal equation:

$$\log S = \log S_0 - T_E/T_2^*. \quad (1)$$

Mean image noise was estimated from an imaging volume outside the body separately for each echo and incorporated into the model regression, and parameter covariance matrices were computed using standard propagation of uncertainty.

Spatial Modeling of $T_2^*$ Distributions

It is well known that arterial and venous blood manifest significantly different transverse relaxation times, with shortening in venous blood due to the paramagnetism of deoxyhemoglobin; this is the basis of the much-studied BOLD effect (Ogawa S, et al, *Proc Natl Acad Sci USA* 87, 9868-9872 (1990); incorporated by reference herein). It is assumed that a pattern of high-to-low $T_2^*$ observed with increasing spatial distance from the spiral artery source within individual perfusion domains in the placenta represents a high-to-low gradient in oxygen concentration in maternal blood within the intervillous space. In this example, a mathematical model relating the spatial distribution of $R_2^*$ (=$1/T_2^*$) within a perfusion domain to relevant underlying physiological parameters is developed. This model predicts the spatial variation of $R_2^*$ as a function of distance from the spiral artery supplying oxygenated blood from the mother to the fetus.

Each lobule is approximated as a spherical perfusion domain supplied with oxygenated maternal blood by a spiral artery located at its center. Further, the flow of maternal blood through the intervillous space of the lobule is assumed to be incompressible, with laminar transport from the central source to venous sinks located at the periphery. Mass conservation can then be used to express the radial displacement ($\rho$) of a parcel of maternal blood as a function of time. Assuming a spiral artery source from which blood is supplied at a rate $\Phi$ (ml/min), and a spatially-uniform volume fraction of intervillous space, $v_i$, the radius at which a Lagrangian element of flowing blood is located increases as $$\frac{d\rho}{dt} = \frac{\Phi}{4\pi\rho^2 v_i}. \quad (2)$$

Assuming conventional first order rate kinetics for the transport of oxygen from the intervillous space to the fetal blood (Faber J, et al, 1983 supra), the rate of change in oxyhemoglobin ($[Hb_o]$) in the intervillous space can be expressed as a function of time as $$\frac{d[Hb_o]}{dt} = -PS([Hb_o] - [Hb_{o,f}]), \quad (3)$$

where PS is the permeability-surface area product for oxygen exchange from the intervillous space to the fetal villi, and $[Hb_{o,f}]$ is the effective (corrected for the increased oxygen affinity of fetal hemoglobin) concentration of oxyhemoglobin in the fetal arterial blood, assumed to be constant within each lobule. Use of the chain rule $$\frac{d[Hb_o]}{d\rho} = \frac{d[Hb_o]}{dt}\frac{dt}{d\rho} \quad (4)$$

yields a first-order differential equation $$\frac{d[Hb_o]}{d\rho} = -PS([Hb_o] - [Hb_{o,f}])\frac{4\pi\rho^2 v_i}{\Phi} \quad (5)$$

that can be solved directly:

$$[Hb_o](\rho) = [Hb_{o,f}] + ([Hb_{o,in}] - [Hb_{o,f}])e^{-\frac{4\pi PS}{3\Phi}v_i\rho^3}, \quad (6)$$

where the integration constant, $[Hb_{o,in}]$, is the maternal oxyhemoglobin concentration at the spiral artery input to the lobule.

In order to express $[Hb_o]$ in terms of $R_2^*$, the observation of Blockley et al. (Bockley, N, et al, *Magn Reson Med* 60, 1313-1320 (2008); incorporated by reference herein) that the $R_2^*$ of blood at a magnetic field strength of 3T depends linearly on deoxyhemoglobin concentration ($[Hb_d]$) is used:

$$R_2^* = R_{20}^* + r_2^*[Hb_d] = R_{20}^* + r_2^*([Hb] - [Hb_o]) \quad (7)$$

with $R_{20}^*$ being the intrinsic $R_2^*$ in the absence of $Hb_d$ and $r_2^*$ the relaxivity of $Hb_d$, reported to be 20.2 $s^{-1}$ $mM^{-1}$ in human blood (Blockley, et al, 2008 supra). Combining the two equations above yields an expression for the radial dependence of $R_2^*$:

$$R_2^*(\rho) = (R_{20}^* + r_2^*([Hb] - [Hb_{o,f}])) + r_2^*([Hb_{o,f}] - [Hb_{o,in}])e^{-\frac{4\pi PS}{3\Phi}v_i\rho^3}. \quad (8)$$

In principle, using [Hb] values obtained from maternal blood draws, [$Hb_{o,in}$] from maternal arterial pulse oximetry, and the experimental $r_2^*$ value for deoxyhemoglobin, this equation can be fit to measured data to estimate $R_{20}^*$, [$Hb_{o,f}$], and $v_iPS/\Phi$ for individual perfusion domains within the placenta. In principle, stereology-based estimates of $v_i$ could also be incorporated to determine the unscaled ratio $PS/\Phi$. However, in the present example, the scaled parameter $v_iPS/\Phi$ is reported because lobule-specific v values were not determined.

A Numerical Algorithm for Spatial Modeling of $R_2^*$ Distributions

In order to describe 3D measured data with this model, an algorithm has been developed and implemented in MATLAB (Mathworks, Natick, Mass.) that reduces the 3D measurements of $R_2^*$ to a single effective dimension. This algorithm proceeds as follows, where specific MATLAB functions are indicated in italics:

(1) A separate mask is created to delineate each lobe of the placenta. Regions of interest (ROIs) are initially drawn on axial T2 HASTE images, then resampled and overlaid on $T_2^*$ maps. Particular care is taken to exclude regions of amniotic fluid and uterine wall from these ROIs.

(2) The $T_2^*$ map derived from fitting the multiecho data and the placenta masks from step (1) are linearly interpolated to 0.75 mm isotropic spatial resolution using interpn with the cubic spline algorithm. This facilitates smoother evolution of the wavefronts computed in step (5).

(3) Local maxima within the placenta are identified in a smoothed version of the interpolated $T_2^*$ map (3D gaussian convolution with a 3 voxel kernel width) using the imregionalmax function.

(4) $N_i$ (i=1,2) lobules in each lobe are identified with the maxima found in step (3), and the locations of these maxima are chosen as seed points.

(5) Iteration number maps, corresponding to approximate isosurfaces, are generated from the interpolated $T_2^*$ map via the multistencil fast marching (MSFM) algorithm (Hassouna M, et al, *IEEE Trans Patt Anal Mach Intel* 29, 1563-1574 (2007); Van Uitert R, et al, *Med Phys* 34, 627-638 (2007); incorporated by reference herein), as implemented in Mathworks File Exchange submission #24531 by Dirk-Jan Kroon. MSFM is run separately for each lobe, initialized with the $N_i$ seed points from step (4).

(6) Each lobe is segmented into $N_i$ perfusion domains by running the watershed segmentation algorithm on the iteration number maps computed in step (5).

(7) Histograms of perfusion domain volume (V), median Euclidean distance from the nearest seed point ($\rho_{eff}$), and median $R_2^*$ (=$1/T_2^*$) are computed as functions of iteration number. For each lobule, iteration number is histogrammed into 100 bins (empirically chosen based on observed data) ranging from 0 to the $95^{th}$ percentile within that lobule. Uncertainty in $R_2^*$ is estimated from the interquartile range of $R_2^*$ values in each histogram bin.

(8) Median $R_2^*$ is plotted against $\rho_{eff}$ out to an empirically chosen cutoff distance of 1.5 cm and Eq. 8 is fit to the resulting curves using weighted nonlinear least squares regression (lsqcurvefit).

DCE-MRI Analysis

DCE-MRI data are processed using the methods described previously (Friar A E, et al, 2015 supra). Briefly, time curves of measured signal intensity are converted to estimates of CR concentration as described in (Schabel M, *Magn Reson Med* 68, 1632-1646 (2012); incorporated by reference herein). Pre-injection longitudinal relaxation time ($T_{10}$) is estimated using the variable flip angle (VFA) method with flip angles of 3° and 25° (Schabel M, 2009, supra), and the full nonlinear relationship between relative signal enhancement ($\Xi$) and concentration (C) is numerically inverted using measured field-dependent relaxivity values (Rohrer M, et al, *Invest Radiol* 40, 715-724 (2005); incorporated herein by reference) to generate time curves of CR concentration (Schabel M, 2012 supra). The arterial input function (AIF) is measured in the inferior abdominal aorta, just above the iliac bifurcation. For the data acquisition geometry in the present study, this location minimizes potential inflow artifacts and partial-volume effects, and was found to provide consistently reliable measurements. Resulting concentration-time curves for each voxel are fit using weighted nonlinear regression to the Gamma Capillary Transit Time (GCTT) model (Schabel M, 2012 supra). Maps of the model tissue blood flow parameter, $F_T$ (=$C_t(t)/(R(t)*C_b(t))$), are resampled and interpolated to match the resolution of the interpolated $T_2^*$ maps, and local maxima in $F_T$, corresponding to spiral artery sources, are identified using the same algorithm as described in step (3) above. It is important to note that $F_T$ represents the instantaneous flow in each individual voxel rather than the total spiral artery flow, which is denoted $\Phi$. While it is theoretically possible to derive the latter from the former, there are a number of technical and practical difficulties, and a derivation is not attempted here. Instead, $F_T$ is simply the scale factor between the tissue concentration curve and the impulse response to the input function. There are two principal advantages to using $F_T$ instead of working directly with a purely descriptive quantifier such as early relative enhancement: (1) the modeling procedure automatically compensates for differences in contrast arrival time between lobules, and (2) the model fitting procedure regularizes the time curves, decreasing sensitivity to motion artifacts arising from respiration.

3D point clouds of image maxima determined separately from the interpolated $T_2^*$ and interpolated $F_T$ maps were co-registered using the iterative closest point (ICP) algorithm (MATLAB File Exchange submission #27804 by Jakob Wilm). The resulting affine transformation was used to estimate both center-of-mass separation (translation) between point clouds and mean between-point separation, compensating for misregistration due to respiratory motion in the DCE-MRI acquisition and allowing us to quantify the spatial concordance between local maxima in transverse relaxation time and in contrast uptake.

Results

Figure 3:
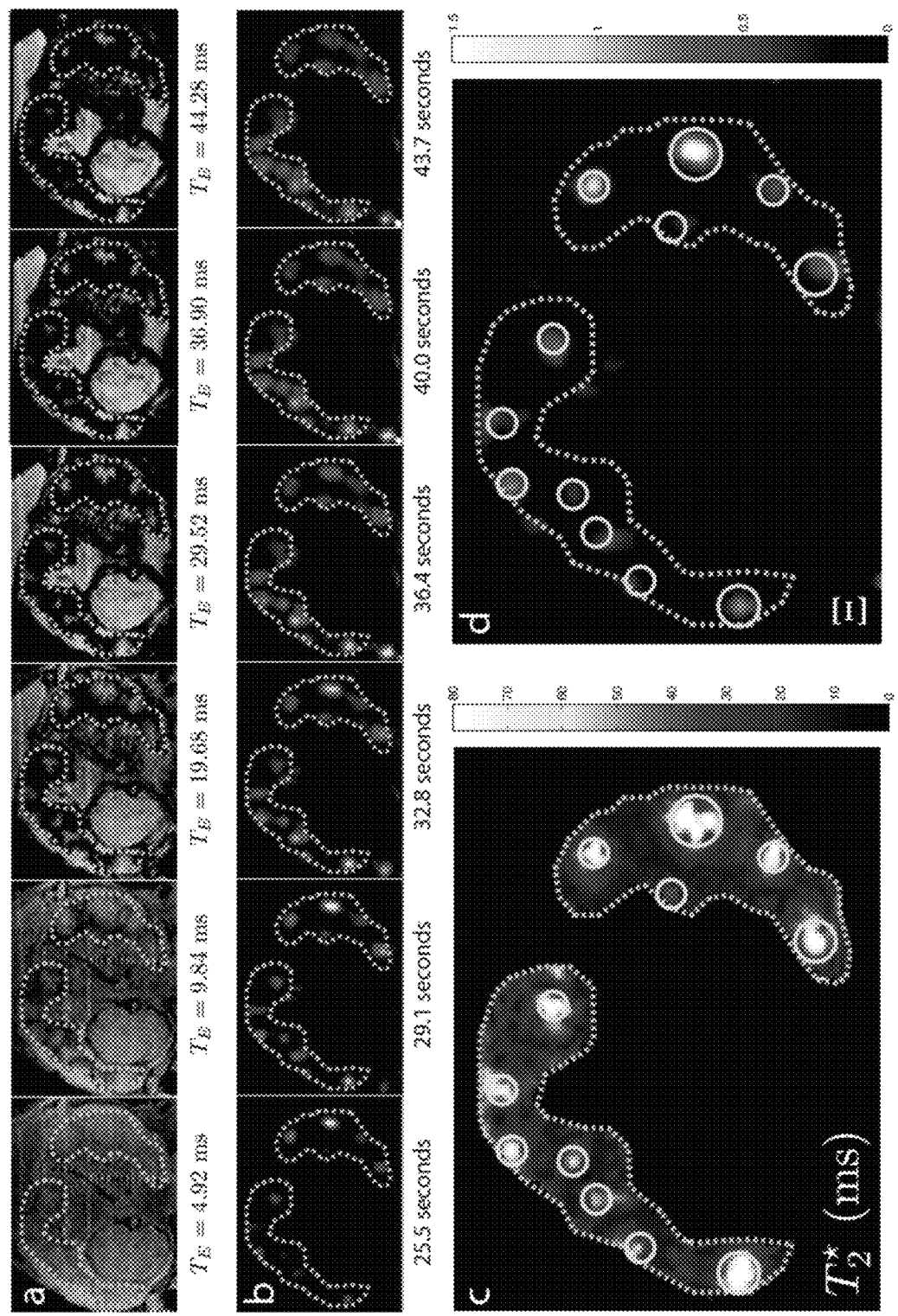
FIG. 3 is a panel of images depicting a comparison of multiecho $T_2^*$ imaging and DCE-MRI results for a single imaging slice through both placental lobes of Animal B. Panel (a) shows signal magnitude for each of the 6 echo times acquired for $T_2^*$ measurements, with TE ranging from 4.92 ms for the first image to 44.28 ms for the last image. Panel (b) plots relative enhancement, $\Xi(t)$, from DCE-MRI measurements for six sequential time points ranging from initial contrast arrival at 25.5 seconds to 43.7 seconds after injection of Gd-based contrast reagent. Panel (c) displays the $T_2^*$ map derived from regression to the data in panel (a), with local maxima in $T_2^*$ indicated by blue circles. Panel (d) shows a magnified and rescaled view of the relative enhancement data at 25.5 seconds post-injection, with $T_2^*$ maxima from panel (c) overlaid without image registration. In all images, placental lobes are delineated by green dashed lines, with the primary lobe on the left and the secondary lobe on the right.

Raw signal measurements for a single axial slice through both placental lobes for each of the six echo times of the multiecho acquisition in animal B are shown in the top panel of FIG. 3, with the boundaries of each lobe indicated by the dashed green lines. The fetal brain is visible in the lower left corner of these images. The acquisition is heavily proton-density weighted for the shortest echo time (4.92 ms), resulting in relatively little contrast between the placenta, fetus, and surrounding tissues, or within the placenta itself. However, inspection of images acquired at progressively longer echo times reveals substantial spatial heterogeneity within the placenta, with focal regions of minimal signal attenuation surrounded by a penumbra of rapidly decreasing signal.

Comparison of the spatial location of foci seen in the later echoes of the multiecho data immediately reveals a high degree of spatial correlation with foci of contrast enhancement observed by DCE-MRI. Relative signal enhancement with CR injection is defined as $\Xi(t)=(S(t)-S_0)/S_0$, where the temporal signal in a voxel is $S(t)$ and the mean baseline signal, averaged over the 10 time points prior to CR injection, is $S_0$. In panel b of FIG. 3, $\Xi(t)$ is shown for six consecutive time points at the same axial position as FIG. 3a. In FIG. 3b, the $\Xi$ maps have been spatially resampled to match the multiecho measurements, with the two placental lobes indicated by the green dashed curves. The initial arrival of contrast to spiral artery outlets within the placenta is apparent, with localized foci in the first time frame slowly evolving outward as contrast-bearing maternal blood perfuses the intervillous space.

To further emphasize the spatial correlation between multiecho measurements and DCE-MRI measurements, the $T_2$* map resulting from fitting multiecho data is shown in FIG. 3c and compared with an expanded map of $\Xi$ at 25.5 seconds post-injection shown in FIG. 3d. The local maxima in $T_2$* are indicated with light blue circles and the same locations are shown, without image registration, on the $\Xi$ map. Maxima in DCE-MRI contrast enhancement correlate extremely well with maxima in transverse relaxation time. However, due to the fact that the multiecho images were acquired during breath-holding while the DCE-MRI data were acquired in the presence of motion arising from maternal respiration, a certain degree of misregistration arising from respiratory motion of the diaphragm and abdomen is expected.

Figure 4:
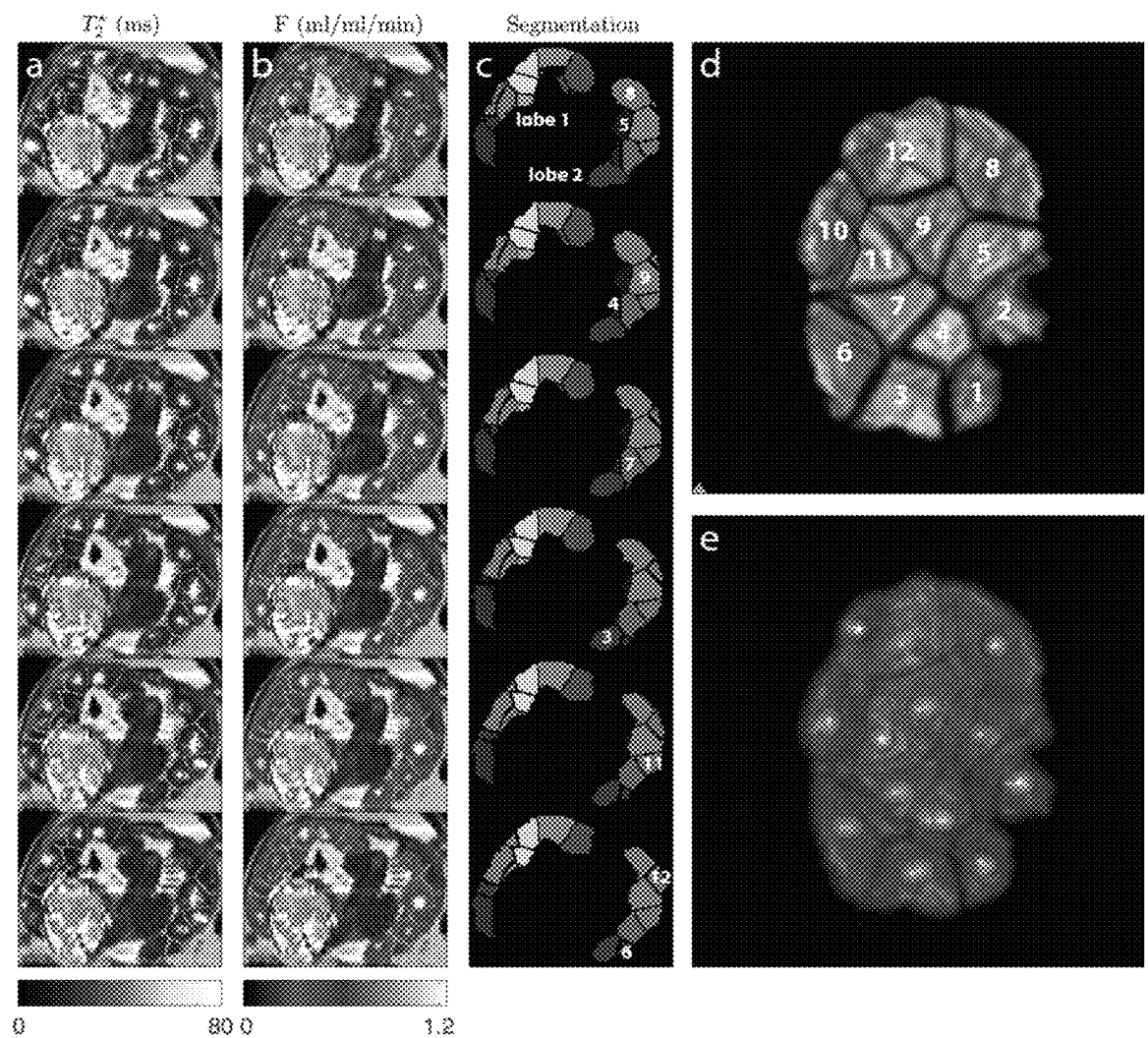
FIG. 4 is a panel of images depicting segmentation of placental $T_2^*$ measurements. Panel (a) displays $T_2^*$ for six sequential slices from Animal B, beginning from the top with the slice shown in FIG. 3. Boundaries between individual lobules, as determined by the segmentation algorithm described in Methods, are indicated in green. Panel (b) shows the tissue blood flow parameter ($F_T$), determined from nonlinear regression to DCE-MRI measurements, for the same six slices. Segmentation boundaries are shown in green. Panel (c) plots the lobule segmentation domains, with domains in the secondary lobe that are visible in these slices numerically labeled for comparison with curves in FIG. 5. These domains are shown as isosurfaces for the entire secondary lobe in panel (d). Panel (e) shows a volume rendering of the secondary lobe, oriented as in panel (d), with local maxima in $T_2^*$ indicated by gray spheres and local maxima in $F_T$ indicated by red spheres. In one lobule a discrepancy is observed between the two measurements, indicated by the asterisks, with two maxima in $F_T$ identified within lobule #12 and none identified within lobule #11. The origin of this discrepancy is discussed further in the text.

FIG. 4a displays $T_2$* maps for six contiguous axial slices through both lobes of the placenta in animal B beginning with the slice shown in FIG. 3. FIG. 4b shows the corresponding maps of $F_T$ derived from model fitting to the DCE-MRI data. Boundaries between placental lobules, determined by watershed segmentation of the smoothed relaxation time maps, are indicated in bright green. The watershed segmentation domains corresponding to placental lobules are shown in the third column, with several of the lobules in lobe 2 numbered. These numbers correspond to lobule numbers in the upper right panel, which displays a volume rendering of the entirety of lobe 2 viewed from the interior of the uterus. The lower right panel is a volume rendering of lobe 2 showing seed points, with spheres of 3 mm radius superimposed on local maxima of the $T_2$* map (gray) and the $F_T$ map (red). Starred maxima indicate the single case where a local maximum in $F_T$ did not closely coincide with a nearby maximum in $T_2$*. In this case, $F_T$ and $T_2$* maxima are not centered on the same placental structure, due to misregistration arising from respiratory motion in the DCE-MRI acquisition. Averaged over all 34 lobules identified for animal B, the mean distance between local maxima in the $T_2$* map and the $F_T$ map is 2.34 mm (minimum/maximum of 0.60 mm–10.5 mm).

Model Fits to Measured Placental $R_2$*

Figure 5:
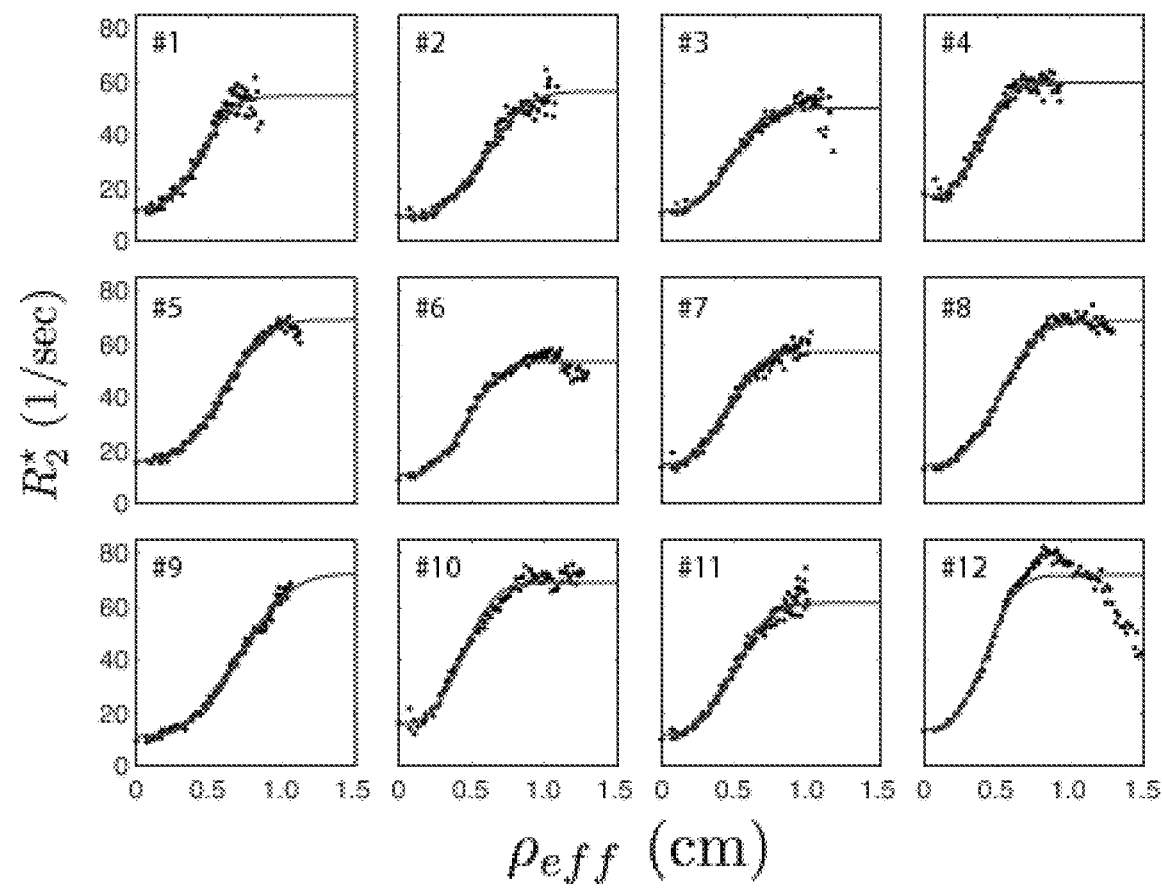
FIG. 5 is a set of plots showing the spatial dependence of measured $R_2^*$ along with model fitting results. Black points show the measured median value of $R_2^*$ as a function of median distance from the central spiral artery for all 12 lobules in the secondary placental lobe of Animal B, as numbered in panel (d) of FIG. 4. Red curves are the results from nonlinear regression to Equation 8.

In order to quantitatively characterize the spatial patterns observed in $R_2$*, data were fitted to Eq. 8. In FIG. 5, the dependence of measured $R_2$* for each lobule in lobe 2 of animal B is plotted against effective radius, $\rho_{eff}$, computed using the algorithm described above. Each of the twelve curves plotted in FIG. 5 correspond to lobule's numeric label in FIG. 4. Model fits (red curves) are shown superimposed on the measured points (black). From the figure, it is clear that Eq. 8 closely approximates the observed changes in $R_2$* as a function of distance from the spiral artery source of maternal blood to each lobule.

Figure 6:
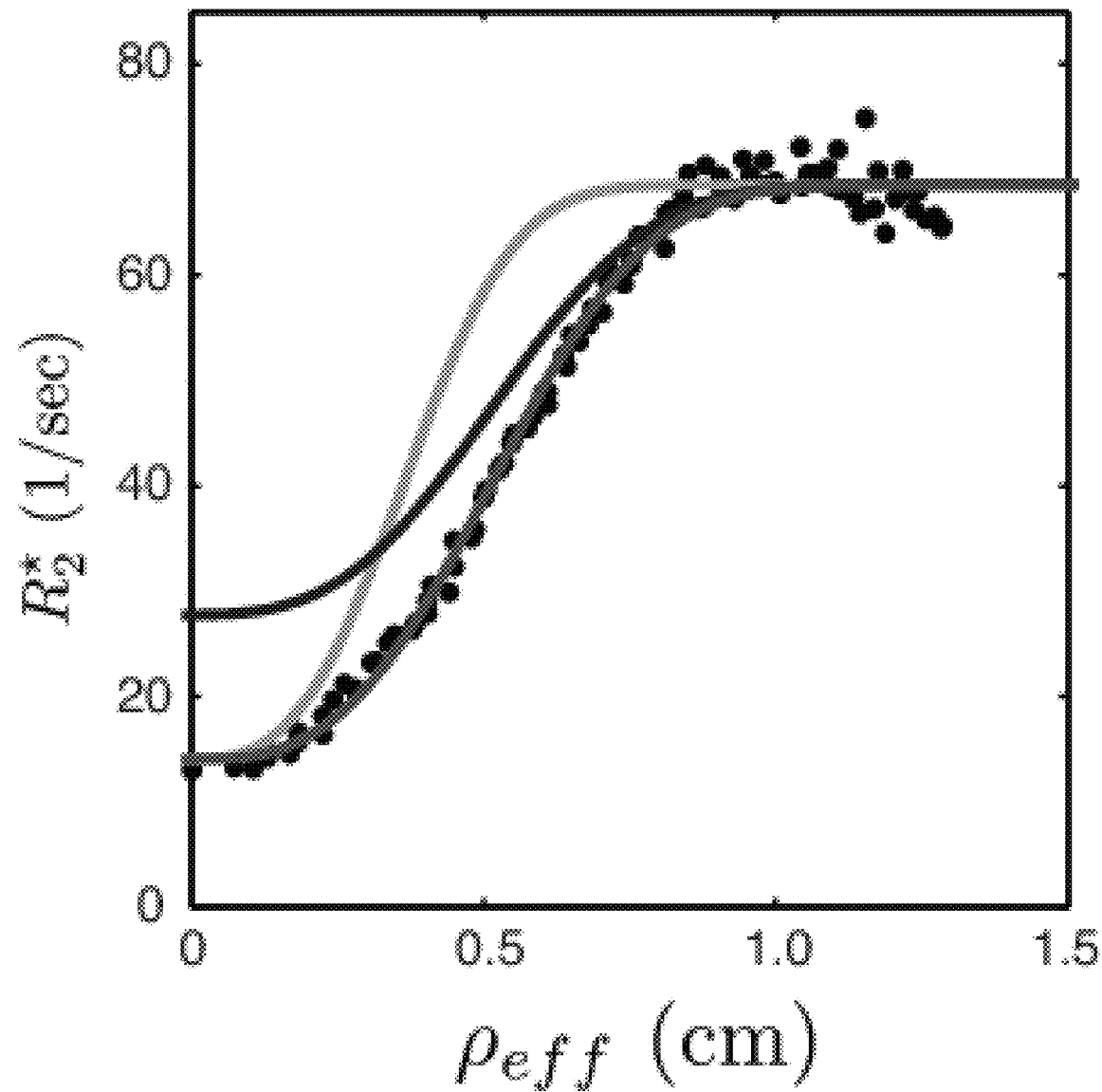
FIG. 6 is a plot showing the sensitivity of the spatial variation in $R_2^*$ to changes in spiral artery blood flow and maternal oxygen saturation for the disclosed model. Black points plot the measured data for lobule #8 from FIG. 5, along with the model fit (red). The blue and green curves plot model predictions for changes in the spatial dependence of $R_2^*$ with a decrease in maternal SpO2 from 100% to 80% (blue) or a decrease of 40% in the spiral artery blood flow (green) to this lobule.

A motivation for the disclosed spatial modeling approach is to provide a means of interpreting $R_2$* in terms of physiological parameters relevant to placental function. FIG. 6 demonstrates the predicted effects of changes in maternal blood flow and maternal blood oxygen saturation on the spatial distribution of $R_2$*. A magnified view of the data from lobule #8 of animal B is shown, with the model regression to the measured data points again indicated by the red curve. The blue curve shows the model prediction for a decrease in maternal $S_pO_2$ from 100% to 80%, resulting in an increase in maternal arterial blood $R_2$*, the y-intercept in FIG. 6. Similarly, the green curve simulates the effect of a reduction in the total blood flow, $\Phi$, to this lobule by 40%, resulting in an increase in the steepness of the dependence of $R_2$* on distance from the spiral artery. Conversely, an increase in spiral artery blood flow decreases the steepness of the $R_2$* curve (not shown).

Measurements performed on two additional animals provide further evidence of correspondence between patterns of $T_2$* and $F_T$ contrast in spite of considerable inter-animal variability in the number of lobules identified, as well as in the observed $R_2$* dependencies on $\rho_{eff}$ anticipated in the simulations shown in FIG. 6. Placentas in animals A and C possessed 18 and 13 lobules, respectively, substantially fewer than the 34 lobules found in animal B. However, the placenta volumes of 78.8 cm$^3$ and 99.4 cm$^3$ for animals A and C were similar to that of animal B (75.8 cm$^3$, Table 1). As a result, lobules were substantially larger in animals A and C than in animal B. Nevertheless, strong correspondence was observed between $T_2$* and $F_T$ parameter maps, with the mean distance between local maxima obtained from the ICP algorithm being 3.17 mm and 6.11 mm for animals A and C, respectively. Mean lobule volume, averaged over both placental lobes for all three animals studied here, is 3.91 cm$^3$, corresponding to a sphere with 0.98 cm radius.

Figure 7:
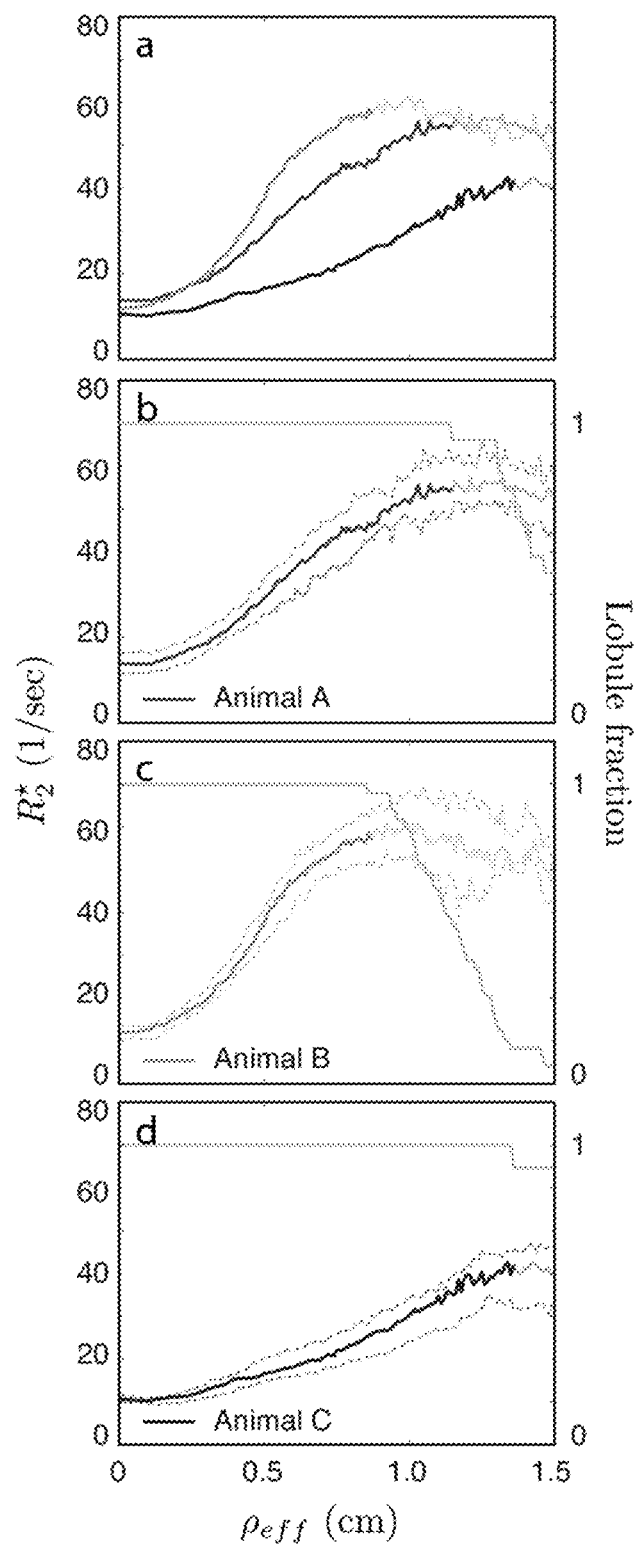
FIG. 7 is a panel of four plots showing the spatial dependence of measured $R_2^*$ for three animals studied using the methods described herein. Panel (a) plots the median dependence of $R_2^*$ on median distance from the spiral artery, averaged over all lobules in both placental lobes, for Animals A (red), B (green), and C (blue). Panels (b)-(d) show the same median curves along with 25%/75% bounds (dashed lines). Median curves are desaturated for distances beyond the maximum radius of the smallest lobule in each animal. Gray curves in panels (b)-(d), corresponding to the right hand axis, show the fraction of lobules having a minimum radius at least as large as $\rho_{\mathit{eff}}$.

In FIG. 7a, the median $R_2$* for voxels in all lobules is plotted versus $\rho_{eff}$ for all three animals (animal A in red, animal B, displayed in FIGS. 3-6, in green, and animal C in blue). FIGS. 7b-d plot $R_2$* versus $\rho_{eff}$ for each of the three animals separately, animal A in 7b (red), animal B in 7c (green), and animal C in 7d (blue). Solid curves show the median $R_2$* averaged over all lobules, with $25^{th}$ and $75^{th}$ percentile curves indicated by dashed lines. Because lobules have different sizes, not every lobule extends to the maximum $\rho_{eff}$ value of 1.5 cm shown in this plot. As a result, the average curves will no longer include smaller lobules at larger effective distances. To clarify this, median curves are desaturated for $\rho_{eff}$ larger than the maximum $\rho_{eff}$ for the smallest lobule in each animal, so that the fully saturated curves include all lobules out to the maximum effective radius of the smallest lobule. The axes on the right side in FIGS. 7b-d correspond to the gray curves, showing the fraction of lobules in each animal that are at least as large as $\rho_{eff}$; curves of $R_2$* are desaturated once this fraction decreases below 1. Most noticeable in comparisons between the three animals are the differences in the spatial gradient of $R_2$* with $\rho_{eff}$, with animal B possessing the steepest curve, animal A being intermediate, and animal C exhibiting the least steep increase in $R_2^*$ with $\rho_{\mathit{eff}}$.

Figure 8:
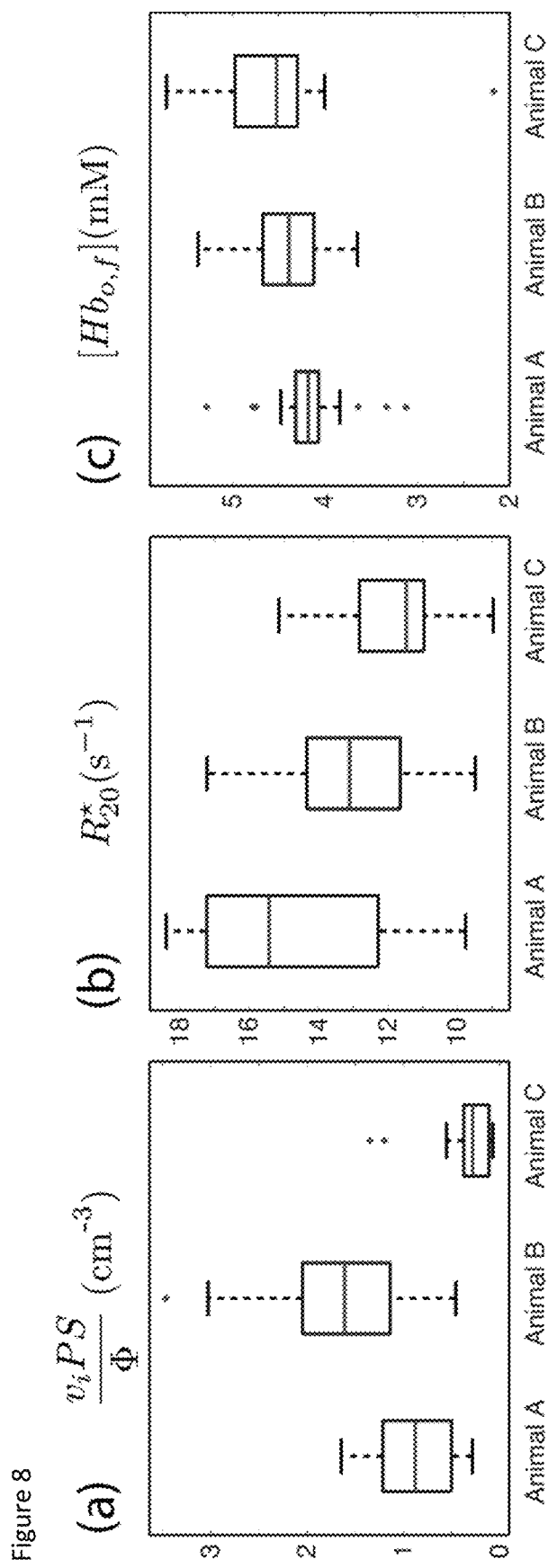
FIG. 8 is a panel of three Box plots of model parameter estimates for three animals studied using the methods described herein. Parameters for all lobules of both placental lobes are included. Panel (a) shows $v_i PS/\Phi$, panel (b) shows $R_{20}^*$, and panel (c) shows $[Hb_{o,t}]$, with Animal A on the left, Animal B in the middle, and Animal C on the right in each panel.

FIG. 8 presents box plots for the three different physiological parameters estimated from the spatial model developed herein in each of the three animals. FIG. 8a shows $v_iPS/\Phi$ estimates for all lobules in each of the three animals. T-tests reveal statistically significant differences in the mean $v_iPS/\Phi$ between animals A and B (p=0.0002), animals A and C (p=0.002), and animals B and C (p<1e-6). In addition, more subtle differences between animals are observable in the y-intercept of FIG. 7a. Model estimates of $R_{20}^*$ for each animal are shown in FIG. 8b. T-tests for differences between animals A and B, A and C, and B and C give p-values of 0.01, 0.001, and 0.03, respectively. Finally, model estimates of $[Hb_{o,f}]$ are shown in FIG. 8c. No statistically significant differences were observed in this parameter between any of the animals. Statistically significant differences were also not observed between the primary and secondary placental lobes for any of the fitted parameters (data not shown). Data obtained for all three animals are summarized in Table 1.

lobule structure evident in $R_2^*$ maps is the same as the structure observed following CR administration into the maternal vasculature. This advance enabled the development of the quantitative framework described herein for interpreting $R_2^*$ measurements in terms of physiological parameters reflecting maternal placental perfusion. It is further noted that similar structures are visible in $T_2^*$-weighted HASTE anatomic imaging in these animals, suggesting that, while non-quantitative, these data, which are commonly used for imaging in pregnancy, can provide a simple means of assessing the functional viability of perfusion domains within the placenta.

Among the three animals characterized in this study, notable variability was observed in the number of lobules identified per placenta, the median $v_iPS/\Phi$ ratio, and the median $R_{20}^*$. These animals were clinically-normal rhesus macaques, assessed at the same day of pregnancy (G110 of a 165 day gestation), and thus the variability observed in this study may reflect the distribution of parameters observable in normal rhesus pregnancy at this gestational age. For each

TABLE 1

MRI- and model-derived placental parameters, along with maternal and fetal physiological parameters

| Animal | Placenta volume ($cm^3$) | # of lobules | Median $v_iPS/\Phi$ ($\times 10^6$ $cm^{-3}$) | Median $R^*_{20}$ ($s^{-1}$) | Median $[Hb_{o,f}]$ (mM) | Arterial $O_2$ saturation (%) | Pulse rate (bpm) | $[Hb_f]$ (mM) | $[Hb_m]$ (mM) |
|---|---|---|---|---|---|---|---|---|---|
| A | 78.8 | 18 | 0.88 ± 0.41 | 15.4 ± 2.6 | 4.17 ± 0.50 | 99.5 | 117 | 7.82 | 6.15 |
| B | 75.8 | 34 | 1.61 ± 0.73 | 13.1 ± 1.9 | 4.39 ± 0.43 | 99.5 | 105 | 7.95 | 6.77 |
| C | 99.4 | 13 | 0.28 ± 0.41 | 11.5 ± 1.7 | 4.52 ± 0.89 | 100 | 108 | 9.44 | 6.21 |

Discussion

This study establishes for the first time a direct correspondence between regional patterns of water $T_2^*$ contrast and spiral artery perfusion territories, identified by DCE-MRI, in the primate placenta. Endogenous, water spin-relaxation-based patterns of MRI contrast similar to the regional pattern of $R_2^*$ examined here have been seen in previous studies of human subjects performed by other researchers. In the $R_2^*$-weighted images of Sorensen and colleagues (Sorensen A, et al, *Ultrasound Obstet Gynecol* 42, 310-314 (2013); incorporated by reference herein) and others (Huen I, et al, *Magn Reson Med* 70, 1427-1433 (2013); incorporated by reference herein) (in the former study, the authors referred to the data as "BOLD images") as well as the $R_2$-weighted images of Derwig et al. (Derwig I, et al, *Placenta* 34, 474-479 (2013); Derwig I, et al, *Placenta* 34, 885-891 (2013); both incorporated by reference herein), approximately six ~3 cm diameter structures are intersected in axial images of the placenta, and within each structure, a high-signal intensity core is surrounded by a low-intensity rim. In a study of murine placenta (which is morphologically quite unlike primate placenta), Bobek et al. (Bobek G, et al, *PLoS One* 8, e59971 (2013), incorporated by reference herin) observed that $T_2$ contrast within the placenta was abolished on elimination of blood flow through terminal anesthesia. Although these results are consistent with the present observation of gradients in $[Hb_d]$ that underlie the quantitative framework proposed herein for interpreting $R_2^*$ parameter maps, these previous analyses did not attribute the observed spatial patterns to the detailed placental vascular organization. It is the combination of quantitative $R_2^*$ determinations with DCE-MRI-based delineation of spiral artery locations in nonhuman primate subjects (Frias A E, et al, 2015 supra) that has enabled the verification that the of the animals, the number of lobules identified by MRI (18, 34, and 13, respectively for animals A, B, and C, Table 1) was consistently larger than the number of cotyledons identified by observers blinded to the MRI data following Cesarean section delivery (9, 13, and 9, respectively for animals A, B, and C) following previously-described procedures (Frias A E, et al, 2015 supra). Imperfect correspondence between the pattern of perfusion domains identified by DCE-MRI and the cotyledons observed following delivery was noted in a previous study in rhesus macaques (Frias A E, et al, 2015 supra). The results presented herein indicate the existence of multiple (as many as 2 to 3) spiral arteries per cotyledon, which is consistent with previous histological examinations of primate placentas.

In addition to variation in the number of lobules, considerable (approximately 5-fold) variation in the median $v_iPS/\Phi$ ratios was also observed between animals. At present, it is not possible to attribute this variability to specific factors within the term $v_iPS/\Phi$. For example, differences between lobules could result from variability in the chorion surface area or permeability to oxygen, the volume fraction of the intervillous space, spiral artery blood flow, or a combination of these factors. It is interesting to note that the number of lobules is inversely related to the median $v_iPS/\Phi$ ratio for this set of animals. The reason for this association is unknown, and future animal studies will focus on identifying correlations between these parameters. However, if it is assumed that the dominant source of variation in this parameter is total blood flow (i.e. that intervillous volume and oxygen permeability are fixed), the sum $\Sigma^\Phi/v_iPS$ can be computed for the entire placenta to estimate normalized total placental blood flow. This sum is $2.03 \times 10^{-5}$ for Animal A, $2.22 \times 10^{-5}$ for Animal B, and $4.86 \times 10^{-5}$ for Animal C, a considerably tighter range than that observed on the lobule level. This suggests that there may be an adaptive relationship between the number of lobules and per-lobule blood flow that regulates total blood flow available to the fetus.

While the model fits the majority of the curves shown in FIG. 6 quite well, lobule #12 appears to be an anomaly, with the model fit becoming relatively poor for values of $\rho_{eff}$ above approximately 0.7 cm accompanied by a pronounced drop-off in $R_2^*$ at larger distances. This particular lobule also corresponds to the single significant discrepancy between local maxima identified in the $T_2^*$ maps and local maxima in tissue blood flow identified from DCE-MRI. Further inspection of the raw image data used to specify the placental region of interest (ROI) revealed that the boundary between the placenta and the uterine wall in this particular anatomic location was relatively indistinct, making the ROI difficult to definitively specify. As a result, some non-placental tissue was likely included when the ROI was drawn, exacerbated by the misregistration between DCE-MRI and $T_2^*$ measurements stemming from the ventilated acquisition (affected by maternal respiratory motion) in the former vs. breath-hold acquisition in the latter. Avid enhancement of the highly vascular uterine wall with contrast administration is consistently observed, so inadvertent inclusion of this tissue can lead to false identification of maxima in the DCE-MRI data. At the same time, uterine wall tissue has a larger $T_2^*$ value (and, consequently, a lower $R_2^*$ value) than the peripheral region of the placental lobules, so inclusion of this tissue within the ROI will simultaneously lead to a spurious drop in $R_2^*$ at larger values of $\rho_{eff}$.

Conclusion

The results of this study demonstrate the presence of focally inhomogeneous regions in maps of $T_2^*$ in non-human primate placenta. Correlation of these regions with the locations of early contrast uptake during injection of gadolinium-based CR further demonstrates that zones of local $T_2^*$ prolongation are spatially congruent with spiral artery sources supplying maternal blood to placental lobules. In order to quantitatively interpret this spatial pattern in terms of placenta physiology, a model has been proposed to connect the observed $T_2^*$ patterns to the parameters $R_{20}^*$, $v_i PS/\Phi$, and $[Hb_{o,i}]$, which relate to intervillous blood flow and oxygen exchange with the fetal vasculature. These data demonstrate the feasibility of using this novel data acquisition protocol and modeling approach quantify placental perfusion with endogenous contrast, simplifying its potential application to human pregnancy. The short acquisition time and lack of CR administration alleviate many of the safety concerns of MRI use during pregnancy.

Example 2

Placental Perfusion and Oxygenation in Zika Virus

The disclosed methods were used to study the effect of Zika virus (ZIKV) infection in a nonhuman primate model as part of a larger study. Specifically, the methods were used to quantify maternal perfusion of the placenta using both Dynamic Contrast-Enhanced MRI (DCE-MRI) imaging to interrogate delivery and transport of maternal blood in the placenta and Blood Oxygen Level Dependent (BOLD) imaging to characterize placental oxygenation (also referred to as T2* imaging). This technique enables the separate quantification of placental perfusion and placental oxygenation while accounting for the complex vascular network of the intervillous space.

Methods

MRI studies were performed on a non-human primate-dedicated 3T Siemens TIM-Trio scanner (Erlangen, Germany) using a circularly-polarized (CP) transmit, 15-channel receive radiofrequency (RF) "extremity" coil (QED, Cleveland, Ohio). For placental MRI, following localization of the placenta and acquisition of $T_2$-weighted half-Fourier acquisition single-shot turbo spin-echo-(HASTE) anatomic images in the coronal and axial planes, axial 2D multislice multiecho spoiled gradient echo (SPGR) images spanning the entire uterus, were acquired. Subsequently, 3D SPGR images were acquired in the coronal plane, also covering the entire uterus, to allow estimation of T1 (longitudinal relaxation time). Immediately after acquisition of VFA data, 150 volumes of 3D SPGR images were acquired for DCE-MRI with intravenous injection of a standard dose of 0.1 mmol/kg of gadoteridol CR (Prohance, Bracco Diagnostics Inc, Princeton, N.J.) at a rate of 30 mL/min using a syringe pump (Harvard Apparatus, Holliston, Mass.), followed by 3D post-contrast SPGR imaging. Anatomic and multiecho imaging was performed during expiratory breath-holding, achieved by temporarily suspending ventilation, while DCE-MRI data were acquired during ventilation. Physiological monitoring of pulse rate, arterial blood oxygen saturation, and end-tidal CO2 partial pressure was performed throughout the imaging study, with no deviations from normal ranges observed in these parameters.

Results

Figure 9:
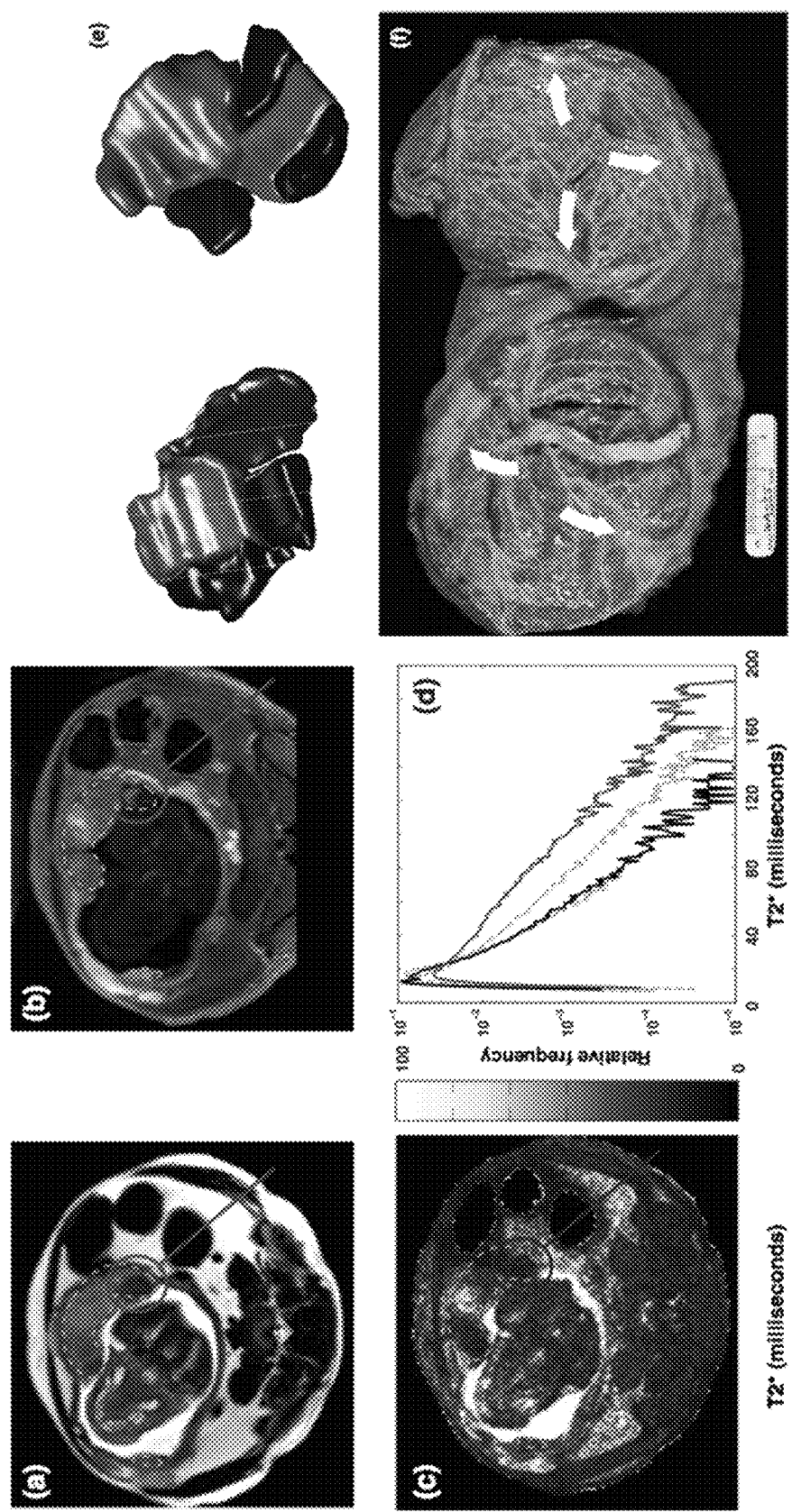
FIG. 9 is a panel of six images showing results obtained using combined in utero BOLD and DCE-MRI imaging of the placenta in a nonhuman primate Zika virus (ZIKV) study. Panel (a) shows an axial T2-weighted HASTE image showing both placental lobes (dashed green lines) and an anomalous dark region (red circle). Panel (b) shows an axial post-contrast GRE image co-registered with the image in panel (a), showing avid contrast uptake within the placenta, excepting a region of hypo-perfused placental tissue corresponding to the dark region in panel (a). Panel (c) shows an axial BOLD $T_2^*$ map co-registered with panels (a) and (b) showing a region of highly oxygenated maternal blood corresponding a spiral artery source (bright spot in the anterior portion of the larger, primary placental lobe) and decreased placental blood oxygen level in the hypo-perfused region. Panel (d) shows a plot of normalized histograms of placental $T_2^*$ values in the ZIKV animal (red line) compared to the median (black line) and 25th/75th percentiles (gray dashed lines) in a cohort of six age matched control animals. Panel (e) shows a volume rendering of the fetal side of the primary (left) and secondary (right) placental lobes, with individual lobules segmented based on the presence of spiral arteries detected on DCE-MRI. Lobules are colored according to total blood flow, with black corresponding to the lowest flow and red to the highest. Dark lobules show markedly decreased flow relative to the brighter ones. Panel (f) shows a photograph of the fetal side of the placenta in the same orientation as the volume rendering in panel (e). Conspicuous light-colored regions of infarcted placental tissue are visible, indicated by white arrows.

When comparing DCE MRI results for one ZIKV infected animal to a group of six pregnant rhesus macaque controls matched at 135dGA, decreases in both total placental blood flow (562 ml/min vs. 662 ml/min, respectively) and normalized placental blood flow (1.73 ml/ml/min vs. 2.23 ml/ml/min, respectively) were found. Histograms of T2* (normalized to placental volume) revealed that the ZIKV infected animal had a significantly higher fraction of oxygenated maternal blood within the placenta as compared to the control group (FIGS. 9c, 9d). The spatial distribution of T2* values within the placenta were modeled using the methods described herein to estimate the ratio of oxygen permeability-surface area product to blood flow. Using these values and flow estimates from DCE-MRI, we found that the oxygen permeability-surface area product (the PS component of the non-dimensional parameter $v_i PS/\Phi$ from Example 1) in the ZIKV infected animal was 3 to 4-fold smaller than in control animals. Given the decreased placental perfusion in this animal, this observation suggests decreased placental oxygen permeability secondary to placental damage. Furthermore, high-resolution post-contrast imaging revealed both gross and scattered punctate regions of placental infarction with no significant contrast uptake (FIGS. 9a and 9b), indicating abnormal perfusion in the placenta from the ZIKV infected dam. Comparison of the 3 dimensional isosurfaces of the primary and secondary lobes generated by MRI analysis, with a photograph of the gross placenta post-delivery showed close correspondence between areas of low perfusion and the infarcted regions (FIGS. 9e and 9f). Of note, the two regions of lowest perfusion correspond to positive sites of ZIKV RNA detection (RNA data not show).

Example 3

Placental Perfusion and Fetal Oxygen Availability in Dietary Protein Restriction The disclosed methods were used to study the effect of malnutrition in a nonhuman primate model. Malnutrition in pregnancy is known to cause fetal growth restriction, stillbirth, and long-term cognitive impairment and neurodevelopmental delay. Dietary protein restriction (PR) or consumption of foods with low-quality proteins, is a form of malnutrition that is common in developing countries. Within the context of PR, the placenta's contribution to obstetric and long-term postnatal complications is not well understood.

The disclosed MRI methods were used to estimate placental oxygen reserve through measurements of $T_2^*$, and perfusion through dynamic contrast enhanced (DCE) MRI. Placental oxygen reserve represents the balance between maternal supply of oxygenated blood and fetal consumption of oxygen. The objective of this study was to evaluate the effects of gestational PR on placental outcomes and to characterize fetal brain development in-vivo. It was hypothesized that gestational PR results in decreased placental function and aberrant fetal brain development.

Study Design

Rhesus macaques were fed a control diet (CON, 26% protein, n=10) or switched to a PR (13% protein, n=10) diet with equivalent essential vitamins and micronutrients before and during pregnancy. All underwent Doppler ultrasound (D-US) followed by MRI procedures that consisted of $T_2^*$ and DCE measurements at gestational day 85 (G85) and G135 (term is G168). D-US was used to measure uterine artery (Uta) and umbilical vein velocimetry and diameter to calculate Uta volume blood flow (cQuta) and placental volume blood flow (cQuv).

Results

Figure 10:
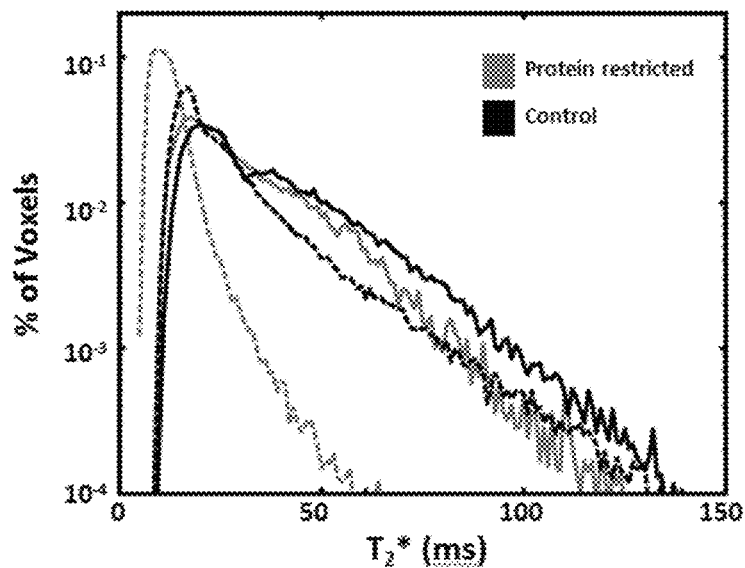
FIG. 10 is a histogram plot of $T_2^*$ versus percent of voxels displayed for protein restriction vs. control animals at G85

Pregnancy rates were 9/10 (CON) and 10/10 (PR) animals with pregnancy loss in 2/9 (CON) and 5/10 (PR). Here we present data from a subset of this cohort, 3 CON animals that carried pregnancy to term vs 3 PR animals that spontaneously aborted. Fetal biparietal diameter, and brain surface area and volume were all reduced at G85 and significantly reduced at G135 in PR vs. CON (Table 1). By D-US, cQuta and cQuv was similar at G85, but was reduced in PR vs. CON at G135. Reductions in placental blood flow were evident by DCE-MRI (Table 2). As demonstrated in the methods disclosed herein, $T_2^*$ values vary throughout the placenta and reveal regions of high oxyhemoglobin concentration (long $T_2^*$) and high deoxyhemoglobin concentration (short $T_2^*$). Distributions of $T_2^*$ throughout the placenta (FIG. 10) show overall reductions in $T_2^*$ (and hence blood oxyhemoglobin) in the PR group relative to controls at G85 and G135. In particular, the reduction in long $T_2^*$ values by G185 in the PR group (denoted by the dashed line) was especially pronounced, along with a notable increase in short $T_2^*$ values (i.e., blood deoxyhemoglobin) at that gestational stage.

Conclusion

Gestational PR results in reduced maternal perfusion of the placenta and fetal oxygen availability contributing to altered fetal brain development. These studies suggest that early maternal diet intervention is necessary to decrease the risk of stillbirth and poor fetal and obstetric outcomes associated with placental dysfunction.

TABLE 2

D-US and MRI-based measurements of fetal biometry and placental function and oxygenation in control (CON) and protein restricted (PR) animals

| Parameter | Gestational day 85 | | Gestational day 135 | |
|---|---|---|---|---|
| | CON (n = 3) | PR (n = 3) | CON (n = 3) | PR (n = 2) |
| Maternal weight (kg) | 7.1 | 5.5* | 7.3 | 5.2* |
| BPD (mm) | 29.1 | 26.2 | 44.6 | 39.4* |
| Brain volume (mm³) | 7566 | 5813 | 32173 | 20950* |
| Brain surface area (mm²) | 2429 | 1961 | 11669 | 6954* |
| cQuta (ml/min/kg) | 17.4 | 18.67 | 15.31 | 13.69 |
| cQuv | 4.6 | 4.7 | 20.5 | 12 |
| Placental blood flow (ml/min) | 717 ± 15 | 412 ± 12 | 808 ± 20 | 518 ± 13 |

Definition of abbreviations:
VTI = velocity time integral,
CSA (cross section of uterine artery) = $\pi(diameter/2)^2$
Vmean (mean velocity) = 0.5 × maximum umbilical vein velocity
cQuta (uterine artery blood flow) = VTI × CSA × HR adjusted for maternal weight
cQuv (placental volume blood flow) = Vmean × CSA × 60
BPD = biparietal diameter
*p < 0.05

Example 4

Placental Perfusion and Fetal Oxygen Availability in Fetal Alcohol Exposure

The disclosed methods were used to study the effect of fetal alcohol exposure in a nonhuman primate model. Alcohol consumption in pregnancy adversely affects fetal growth and development, and can lead to complications such as growth restriction and stillbirth. Prior in vitro studies have suggested that acute ethanol exposure to the placenta induces a pressor effect on placental vasculature, which may decrease fetal oxygen delivery (Taylor S M et al, *Eur J Pharmacol* 270, 371-374, (1994); incorporated by reference herein) but the chronic effects on in-vivo placental perfusion and oxygenation are not known. Although prior studies have used MRI to semi-quantitatively assess placental oxygenation in pregnancy, it has not been quantitated or directly linked to placental perfusion in-vivo. This study utilizes a pregnant nonhuman primate model (NHP) model to assess the effects of first trimester ethanol exposure on placental perfusion using the MRI-based methods disclosed herein and correlate these results with placental blood flow by conventional Doppler ultrasound (D-US).

Methods

Time-mated pregnant macaques (n=6) were divided into 2 treatment groups: control (n=3) and ethanol exposed (n=3). Animals were given either 1.5 g/kg/day of ethanol (equivalent to 6 drinks per day) or an isocaloric control fluid through gestational day 60 (G60, term is 168 days). On G110, all animals were sedated with 1% isoflurane and underwent D-US (GE Voluson 730) followed by MRI. D-US was performed to measure uterine artery and umbilical vein velocimetry and diameter to calculate uterine artery volume blood flow (cQuta) and placental volume blood flow (cQuv) (Acharya G et al, *Ultrsound Obstet Gynecol* 29, 401-406, (2007); incorporated by reference herein). Multi-slice, multi-echo spoiled gradient echo images covering the entire placenta were acquired on a 3T Siemens TIM Trio scanner and were used to compute maps of $T_2^*$. The methods described herein were used to determine the number of spiral artery sources and a parameter $\Psi(=F/v_fPS)$ that is equal to the total spiral artery flow (F) normalized by the product of intervillous volume fraction ($v_i$) and fetal villous oxygen permeability surface area product (PS). The sum of this parameter over all sources, $\Sigma\Psi_i$, was calculated for comparison to uterine artery and placental volume flow values obtained by D-US.

Results

Fetal biparietal diameter (35 vs. 39 cm), cerebral cortex surface area (5970 vs. 6424 mm$^2$) fetal weight (175.1 vs. 217.1 g), and mean placental weight (64 vs. 75 g) were decreased in ethanol exposed animals compared with controls. By D-US, we demonstrated a reduction in cQuta (148 vs. 341 ml/min) and cQuv (15 vs. 22 ml/min) and increased umbilical artery (1.68 vs. 1.22) and uterine artery (0.82 vs. 0.65) pulsatility indices in ethanol exposed animals vs. controls.

MRI confirmed that placental blood flow and fetal oxygen transport was decreased in the ethanol exposed group (Table 3) (FIGS. 11a and 11b). Histograms of $T_2$* computed over the entire placenta (normalized to total placental volume) indicate the fraction of placenta that is perfused with highly oxygenated blood (high $T_2$* values) vs. deoxygenated blood (low $T_2$*values). Control animals demonstrated a significantly greater fraction of higher $T_2$* values compared to the ethanol exposed animals, demonstrating decreased fetal oxygen supply in the latter group (FIG. 12). Moreover, D-US and MRI measurements of maternal perfusion of the placenta (cQuta vs. $\Sigma\Psi_i$) were strongly correlated, r=0.91 (p=0.01) (FIG. 13).

Discussion

D-US detected impaired maternal perfusion of the placenta and increased vascular resistance. The MRI-methods disclosed herein confirmed our D-US findings and were able to quantitate placental oxygenation and directly correlate it with placental perfusion in-vivo. This suggests that cessation of alcohol consumption early in pregnancy does not prevent subsequent adverse fetal affects.

Conclusion

Chronic first trimester prenatal ethanol exposure results in reduced maternal perfusion of the placenta and fetal oxygen availability. Disrupted placental function is associated with impaired fetal growth and development.

TABLE 3

MRI-based measurements of placental function and oxygenation

| Parameter | Control (n = 3) | Ethanol Exposed (n = 3) |
|---|---|---|
| Placental volume (cm$^3$) | 81.6 ± 16.2 | 53.6 ± 6.8 |
| Median $\Psi_i$ (×10$^{-6}$ cm$^3$) | 2.51 ± 2.48 | 0.65 ± 0.23 |
| $\Sigma\Psi_i$ (×10$^{-6}$ cm$^3$) | 40.33 ± 25.35 | 9.57 ± 5.3 |

Definition of abbreviations:
$\Psi$ = fetal oxygen transport,
$\Sigma\Psi_i$ = total spiral artery flow Example 5

In some embodiments, the above described methods and processes may be tied to a computing system, including one or more computers. In particular, the methods and processes described herein, e.g., method 200 described above, may be implemented as a computer application, computer service, computer API, computer library, and/or other computer program product.

FIG. 14 schematically shows a non-limiting computing device 1400 that may perform one or more of the above described methods and processes. For example, FIG. 14 may represent an MRI data acquisition system, an image processing system, and/or any suitable processor which includes circuitry programmed to perform the various operations described herein. Computing device 1400 is shown in simplified form. It is to be understood that virtually any computer architecture may be used without departing from the scope of this disclosure. In different embodiments, computing device 1400 may take the form of a microcomputer, an integrated computer circuit, microchip, a mainframe computer, server computer, desktop computer, laptop computer, tablet computer, home entertainment computer, network computing device, mobile computing device, mobile communication device, gaming device, etc.

Computing device 1400 includes a logic subsystem 1402 and a data-holding subsystem 1404. Computing device 1400 may optionally include a display subsystem 1406 and a communication subsystem 1408, and/or other components not shown in FIG. 14. Computing device 1400 may also optionally include user input devices such as manually actuated buttons, switches, keyboards, mice, game controllers, cameras, microphones, and/or touch screens, for example.

Logic subsystem 1402 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1404 may include one or more physical, non-transitory devices configured to hold data and/or instructions executable by the logic subsystem to implement the herein described methods and processes. When such methods and processes are implemented, the state of data-holding subsystem 1404 may be transformed (e.g., to hold different data).

Data-holding subsystem 1404 may include removable media and/or built-in devices. Data-holding subsystem 1404 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1404 may include devices with one or more of the following characteristics: volatile, nonvolatile, dynamic, static, read/write, read-only, random access, sequential access, location addressable, file addressable, and content addressable. In some embodiments, logic subsystem 1402 and data-holding subsystem 1404 may be integrated into one or more common devices, such as an application specific integrated circuit or a system on a chip.

FIG. 14 also shows an aspect of the data-holding subsystem in the form of removable computer-readable storage media 1412, which may be used to store and/or transfer data and/or instructions executable to implement the herein described methods and processes. Removable computer-readable storage media 1412 may take the form of CDs, DVDs, HD-DVDs, Blu-Ray Discs, EEPROMs, flash memory cards, and/or floppy disks, among others.

When included, display subsystem 1406 may be used to present a visual representation of data held by data-holding subsystem 1404. As the herein described methods and processes change the data held by the data-holding subsystem, and thus transform the state of the data-holding subsystem, the state of display subsystem 1406 may likewise be transformed to visually represent changes in the underlying data. Display subsystem 1406 may include one or more display devices utilizing virtually any type of technology. Such display devices may be combined with logic subsystem 1402 and/or data-holding subsystem 1404 in a shared enclosure, or such display devices may be peripheral display devices. In some embodiments, computing device 1400 may additionally include an audio subsystem including one or more speakers which may be used to present audio representations of data held by data-holding subsystem 1404.

When included, imaging subsystem 1410 may be used acquire and/or process any suitable image data from various sensors or imaging devices in communication with computing device 1400. For example, imaging subsystem may be configured to acquire MRI data as part of an MRI system. Imaging subsystem 1410 may be combined with logic subsystem 1402 and/or data-holding subsystem 1404 in a shared enclosure, or such imaging subsystems may comprise When included, communication subsystem 1408 may be configured to communicatively couple computing device 1400 with one or more other computing devices. Communication subsystem 1408 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 1400 to send and/or receive messages to and/or from other devices via a network such as the Internet.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and non-obvious combinations and subcombinations of the various processes, systems and configurations, and other features, functions, acts, and/or properties disclosed herein, as well as any and all equivalents thereof.

The invention claimed is:

1. A method for quantifying a placental function, the method comprising:

receiving a set of magnetic resonance images, the set of magnetic resonance images depicting endogenous oxyhemoglobin-deoxyhemoglobin contrast data;

identifying a region of interest in the set of magnetic resonance images, wherein the region of interest delineates a placenta;

identifying within the region of interest a plurality of local maxima in the endogenous oxyhemoglobin-deoxyhemoglobin contrast data, wherein each local maximum of the plurality of local maxima corresponds to a site of oxygenated blood inflow from a maternal spiral artery;

defining a plurality of perfusion domains within the region of interest, wherein each perfusion domain of the plurality of perfusion domains encompasses at least one local maximum in the plurality of local maxima and corresponds to an individual lobule of the placenta;

fitting the endogenous oxyhemoglobin-deoxyhemoglobin contrast data from the set of magnetic resonance images within each of the plurality of perfusion domains to a mathematical model described by equations:

$$R_2^*(\rho) = (R_{20}^* + r_2^*([Hb] - [Hb_{o,f}])) + r_2^*([Hb_{o,f}] - [Hb_{o,in}])e^{-\frac{4\pi PS}{3\Phi}v_i\rho^3}$$

where $R_2^*(\rho)$ is a transverse relaxation rate expressed as a function of radial distance $\rho$ from a spiral artery input, $R_{20}^*$ is an intrinsic transverse relaxation rate $R_2^*$ in absence of deoxyhemoglobin $Hb_d$, $r_2^*$ is $R_2^*$ relaxivity of $Hb_d$, $[Hb]$ is a hemoglobin concentration, $[Hb_{o,f}]$ is an effective concentration of oxyhemoglobin in fetal arterial blood, $[Hb_{o,in}]$ is a maternal oxyhemoglobin concentration at a spiral artery input to a lobule, PS is a permeability-surface area product for oxygen exchange from an intervillous space to the fetal villi, $v_i$ is a volume fraction of intervillous space, $\Phi$ is a blood flow rate at a spiral artery input, and $\rho$ is the radial distance; and indicating an estimate of the placental function calculated from the mathematical model.

2. The method of claim 1, wherein indicating the estimate of placental function comprises quantifying fetal oxyhemoglobin concentration and a parameter representing a facility with which oxygen transport from a maternal to fetal vasculature occurs.

3. The method of claim 1, wherein the received set of magnetic resonance images is obtained using a $T_2$-weighted spin-echo pulse sequence.

4. The method of claim 1, wherein the received set of magnetic resonance images is obtained using a multi-echo spoiled gradient echo recalled (SPGR) pulse sequence.

5. The method of claim 1, wherein fitting the endogenous oxyhemoglobin-deoxyhemoglobin contrast data includes computing a transverse relaxation time for each voxel within the region of interest.

6. The method of claim 5, wherein computing the transverse relaxation time is performed by using a weighted least squares regression algorithm to fit equation:

$$\log S = \log S_0 - T_E/T_2^*$$

where $T_2^*$ is the transverse relaxation time, S is a signal intensity, $S_0$ is a baseline signal intensity, and $T_E$ is an imaging echo time.

7. The method of claim 1, wherein defining the plurality of perfusion domain within the region of interest comprises performing using a multistencil fast-marching method, a level set method, an active contour method, or a watershed segmentation method.

8. A system for quantifying a placental function, the system comprising:
   a logic subsystem; and
   a data holding subsystem comprising non-transitory, machine-readable instructions stored thereon that are executable by the logic subsystem to:
   receive a set of magnetic resonance images, the set of magnetic resonance images depicting endogenous oxyhemoglobin-deoxyhemoglobin contrast data;
   identify a region of interest in the set of magnetic resonance images, wherein the region of interest delineates a placenta;
   identify within the region of interest a plurality of local maxima in the endogenous oxyhemoglobin-deoxyhemoglobin contrast data, wherein each local maxim of the plurality of local maxima corresponds to a site of oxygenated blood inflow from a maternal spiral artery;
   define a plurality of perfusion domains within the region of interest, wherein each perfusion domain of the plurality of perfusion domains encompasses at least one local maximum in the plurality of local maxima and corresponds to an individual lobule of the placenta;
   fit the endogenous oxyhemoglobin-deoxyhemoglobin contrast data from the set of magnetic resonance images within each of the plurality of perfusion domains to a mathematical model described by equation:

$$R_2^*(\rho) = (R_{20}^* + r_2^*([Hb] - [Hb_{o,f}])) + r_2^*([Hb_{o,f}] - [Hb_{o,in}])e^{-\frac{4\pi PS}{3\Phi}v_i(\rho)\rho^3}$$

where $R_2(\rho)$ is a transverse relaxation rate expressed as a function of radial distance $\rho$ from a spiral artery input, $R_{20}^*$ is an intrinsic transverse relaxation rate $R_2^*$ in absence of deoxyhemoglobin $Hb_d$, $r_2^*$ is $R_2^*$ relaxivity of $Hb_d$, [Hb] is a hemoglobin concentration, $[Hb_{o,f}]$ is an effective concentration of oxyhemoglobin in fetal arterial blood, $[Hb_{o,in}]$ is a maternal oxyhemoglobin concentration at a spiral artery input to a lobule, PS is a permeability-surface area product for oxygen exchange from an intervillous space to the fetal villi, $v_i$ is a volume fraction of intervillous space, $\Phi$ is a blood flow rate at a spiral artery input, and $\rho$ is the radial distance; and
   indicating an estimate of the placental function calculated from the mathematical model.

9. The system of claim 8, wherein indicating the estimate of placental function comprises quantifying fetal oxyhemoglobin concentration and a parameter representing a facility with which oxygen transport from a maternal to fetal vasculature occurs.

10. The system of claim 8, wherein the received set of magnetic resonance images is obtained using a $T_2$-weighted spin-echo pulse sequence.

11. The system of claim 8, wherein the received set of magnetic resonance images is obtained using a multi-echo spoiled gradient echo recalled (SPGR) pulse sequence.

12. The system of claim 8, wherein fitting the endogenous oxyhemoglobin-deoxyhemoglobin contrast data, the machine-readable instructions, when executed, cause the logic subsystem to use the endogenous oxyhemoglobin-deoxyhemoglobin contrast data in the region of interest to compute a transverse relaxation time for each voxel within the region of interest.

13. The system of claim 12, wherein computing the transverse relaxation time is performed with a weighed linear least squares algorithm to fit equation:

$$\log S = \log S_0 - T_E/T_2^*$$

where $T_2^*$ is the transverse relaxation time, S is a signal intensity $S_0$ is a baseline signal intensity, and $T_E$ is an imaging echo time.

14. The system of claim 8, wherein the plurality of perfusion domain within the region of interest is defined according to a multistencil fast-marching method, a level set method, an active contour method, or a watershed segmentation method.

15. The system of claim 9, further comprising an imaging subsystem configured to acquire the magnetic resonance images.

* * * * *